United States Patent
Picard et al.

(10) Patent No.: US 9,341,704 B2
(45) Date of Patent: May 17, 2016

(54) METHODS AND SYSTEMS FOR OBJECT TRACKING

(76) Inventors: Frederic Picard, Glasgow (GB); Gontje C. Claasen, Charenton-le-Pont (FR); Philippe P. Martin, Paris (FR)

( * ) Notice: Subject to any disclaimer, the term of this patent is extended or adjusted under 35 U.S.C. 154(b) by 565 days.

(21) Appl. No.: 13/640,783

(22) PCT Filed: Apr. 13, 2011

(86) PCT No.: PCT/IB2011/000823
§ 371 (c)(1),
(2), (4) Date: Dec. 3, 2012

(87) PCT Pub. No.: WO2011/128766
PCT Pub. Date: Oct. 20, 2011

(65) Prior Publication Data
US 2013/0064427 A1    Mar. 14, 2013

Related U.S. Application Data

(60) Provisional application No. 61/323,385, filed on Apr. 13, 2010.

(51) Int. Cl.
*G06K 9/00* (2006.01)
*G01S 5/16* (2006.01)
(Continued)

(52) U.S. Cl.
CPC .............. *G01S 5/163* (2013.01); *A61B 19/5244* (2013.01); *A61B 2017/00725* (2013.01); *A61B 2019/4894* (2013.01); *A61B 2019/5248* (2013.01); *A61B 2019/5255* (2013.01)

(58) Field of Classification Search
None
See application file for complete search history.

(56) References Cited

U.S. PATENT DOCUMENTS

| 6,611,141 B1 | 8/2003 | Schulz et al. |
| 6,973,202 B2 | 12/2005 | Mostafavi |
| 7,274,504 B2 | 9/2007 | Crane et al. |

(Continued)

FOREIGN PATENT DOCUMENTS

| DE | 4225112 C1 | 12/1993 |
| WO | 2009/045827 A2 | 4/2009 |

OTHER PUBLICATIONS

Tao, Yaqin, Huosheng Hu, and Huiyu Zhou. "Integration of vision and inertial sensors for 3D arm motion tracking in home-based rehabilitation." The International Journal of Robotics Research 26, No. 6 (2007): 607-624.*

(Continued)

*Primary Examiner* — Sumati Lefkowitz
*Assistant Examiner* — Carol Wang
(74) *Attorney, Agent, or Firm* — Thomas J. Engellenner; Reza Mollaaghababa; Pepper Hamilton LLP

(57) ABSTRACT

Methods and systems for object tracking are disclosed in which the bandwidth of a "slow" tracking system (e.g., an optical tracking system) is augmented with sensor data generated by a "fast" tracking system (e.g., an inertial tracking system). The tracking data generated by the respective systems can be used to estimate and/or predict a position, velocity, and orientation of a tracked object that can be updated at the sample rate of the "fast" tracking system. The methods and systems disclosed herein generally involve an estimation algorithm that operates on raw sensor data (e.g., two-dimensional pixel coordinates in a captured image) as opposed to first processing and/or calculating object position and orientation using a triangulation or "back projection" algorithm.

28 Claims, 9 Drawing Sheets

(51) Int. Cl.
*A61B 19/00* (2006.01)
*A61B 17/00* (2006.01)

(56) References Cited

U.S. PATENT DOCUMENTS

| | | | |
|---|---|---|---|
| 7,594,933 B2 | 9/2009 | Kammerzell et al. | |
| 2004/0135069 A1 | 7/2004 | Odell | |
| 2006/0058604 A1 | 3/2006 | Avinash et al. | |
| 2006/0282873 A1 | 12/2006 | Zalewski et al. | |
| 2007/0034731 A1* | 2/2007 | Falco | 244/3.1 |
| 2007/0078334 A1 | 4/2007 | Scully et al. | |
| 2008/0262772 A1 | 10/2008 | Luinge et al. | |
| 2008/0285805 A1 | 11/2008 | Luinge et al. | |
| 2009/0306509 A1* | 12/2009 | Pedersen et al. | 600/446 |
| 2011/0218546 A1* | 9/2011 | De la Fuente Klein et al. | 606/104 |

OTHER PUBLICATIONS

Brisson, G., et al., "Precision Freehand Sculpting of Bone," MICCAI, LNCS, vol. 3217, pp. 105-112 (2004).
Crassidis, John L., "Survey of Nonlinear Attitude Estimation Methods," Journal of Guidance, Control, and Dynamics, vol. 30, No. 1, pp. 12-28 (Jan.-Feb. 2007).
Grewal, M., et al., "Kalman Filter Basics," Global Positioning Systems, Inertial Navigation, and Integration, pp. 179-228 (2001).
Haider, H., PhD., et al., "Minimally Invasive Total Knee Arthroplasty Surgery Through Navigated Freehand Bone Cutting," The Journal of Athroplasty, vol. 22, No. 4, pp. 535-542 (2007).
Hartmann, B., et al., "Indoor 3D Position Estimation Using Low-Cost Inertial Sensors and Marker-Based Video-Tracking," IEEE, pp. 319-326 (2010).
Hy-Bird, "Hy-Brid Optical/Inertial Tracker: All-Attitude Helmet Tracking Without Occlusions," Ascension Technology Corporation, 2 pages (2005).
International Search Report and Written Opinion for Application No. PCT/IB2011/000823, dated Apr. 11, 2011 (10 pages).
International Preliminary Examination Report for Application No. PCT/IB2011/000823, dated Oct. 26, 2012 (9 pages).
Jurss, U., et al., "Tracking Hot Spots", Elecktor, vol. 383, Nov. 2008.
Kane, G., et al., "System Design of a Hand-Held Mobile Robot for Craniotomy," LNCS, vol. 5761, pp. 402-409 (2009).
Knappe, P., et al., "Position Control of a Surgical Robot by a Navigation System," Intl. Conference of Intelligent Robots and Systems, pp. 3350-3354 (2003).
Parnian, N., "Integration of Local Positioning System & Strapdown Inertial Navigation System for Hand-Held Tool Tracking," A Thesis presented to the The University of Waterloo in fulfillment of the thesis required for the degree of Doctor Philosophy in Electrical and Computer Engineering, Ontario, Canada, 134 pages (2008).
Parnian, N., "Integration of vision and inertial sensors for industrial tools tracking," IEEE, vol. 27(2), pp. 132-141 (2007).
Parnian, N., et al., "Integration of Vision and Inertial Sensors for a Surgical Tool Tracking," Proceedings of IMECE, 7 pages (Nov. 5-10, 2006).
Parnian, N., "Position Sensing Using Integration of a Vision System and Inertial Sensors," IEEE, pp. 3011-3015 (2008).
Parnian, N., "A Low-Cost Hybrid SDINS/Multi-Camera Vision System for a Hand-held Tool Positioning," IEEE, pp. 489-496 (2008).
Polaris Vicra & Spectra—Optical Medical Measurement Systems, http://ndigital.com/medical/polarisfamily.php (2008).
Roetenberg, D., Inertial and magnetic sensing of human motion, University of Twente, 124 pages (2006).
Tao, Y., et al., "Integration of Vision and Inertial Sensors for 3D Arm Motion Tracking in Home-based Rehabilitation," International J. Robotics Research, vol. 26, pp. 607-624 (2007).
Tobergte, A., et al., "Robust Multi Sensor Pose Estimation for Medical Applications," IEEE/RSJ International Conference on Intelligent Robots and Systems, pp. 492-497 (2009).
Umeyama, S., Least-Squares Estimation of Transformation Parameters Between Two Point Patters, IEEE T Pattern Anal vol. 13(4), pp. 376-380 (1991).
Welch, G. et al., "An Introduction to the Kalman Filter," Technical Report RR 95-041 (updated Jul. 24, 2006), University of North Carolina, Chapel Hill, NC 27599.

* cited by examiner

METHODS AND SYSTEMS FOR OBJECT TRACKING

CROSS-REFERENCE TO RELATED APPLICATIONS

This application is a national stage entry of International Application No. PCT/IB11/00823, filed on Apr. 13, 2011, the entire contents of which are incorporated herein by reference. This application also claims the benefit of priority of U.S. Provisional Patent Application No. 61/323,385, filed on Apr. 13, 2010, the entire contents of which are incorporated herein by reference.

FIELD

The present invention relates to methods and systems for object tracking and, in particular, methods and systems for determining the position and orientation of surgical instruments in three-dimensional space to assist in navigated surgery.

BACKGROUND

Real-time monitoring of the position and orientation of handheld and/or fully automated surgical tools has been hampered by a lack of low-cost accurate sensors. Optical tracking, e.g., detection of reflective or light emitting markers associated with the tool, has been proposed but requires clear line of sight to function accurately. Additionally, high bandwidth (high sampling rate) optical sensor systems are often prohibitively expensive. However, less expensive optical systems, for example, those with sampling rates of about 60 Hz, are often unacceptable for guided controlled surgical instruments because they track too slowly. This can make it difficult or impossible to use guided instruments requiring a fast and accurate response, such as a controlled burr or shaver tool. Instead, a cutting guide is often required, the installation and removal of which can unduly lengthen the time duration of the surgery. Electromagnetic tracking systems can also be unacceptable for many of the same reasons.

Inertial sensor systems, e.g., involving sets of three gyroscopes, three accelerometers and optionally, three magnetometers, can inexpensively provide rapidly updated signals indicative of surgical instrument movement. Sampling rates of up to 500 Hz are practical at low cost but such systems are not reliable due to noise and signal drift associated with such inertial sensors.

Hybrid systems combining two or more types of sensors have been proposed by others. See, for example, U.S. Pat. No. 6,611,141 issued to Schulz et al. on Aug. 26, 2003 entitled "Hybrid 3-D Probe Tracked by Multiple Sensors," the entire contents of which are incorporated herein by reference.

There exists a need for better methods and systems for object tracking and, in particular, better methods and systems for determining the position and orientation of surgical instruments in three-dimensional space to assist in navigated surgery. Inexpensive methods and systems that could permit position and movement tracking with rapid updates, e.g., at rates greater than 300 Hz, would satisfy a long-felt need in the art.

SUMMARY

Methods and systems for object tracking are disclosed in which the bandwidth of a "slow" tracking system (e.g., an optical tracking system) is augmented with sensor data generated by a "fast" tracking system (e.g., an inertial tracking system). The tracking data generated by the respective systems can be used to estimate and/or predict a position, velocity, and/or orientation of a tracked object that can be updated at the sample rate of the "fast" tracking system. The methods and systems disclosed herein generally involve an estimation or data fusion algorithm that operates on raw image data (e.g., two-dimensional pixel coordinates in a captured image) as opposed to first processing and/or calculating object position and orientation using a triangulation or "back projection" algorithm. This can advantageously reduce cost, latency, and/or computational overhead of the system as well as, in at least some instances, also increase accuracy.

In a first aspect, a system is provided for tracking motion of an object. The system can include an object comprising a plurality of optical markers rigidly connected to the object, an inertial transmitter for transmitting high speed signals of object movement, and at least one camera for imaging said plurality of markers and generating image data indicative of the object location. The system can also include a receiver for receiving inertial movement signals from the inertial transmitter and a processor for executing an estimation algorithm, the estimation algorithm merging the optically-derived image data and the high speed inertial movement signals to generate estimated motion data at a frequency of at least 300 Hz. In one embodiment, the estimated motion data can include a position of the object, a velocity of the object, and/or an orientation of the object. The estimation algorithm can operate directly on raw image data, and the raw image data can comprise a plurality of two-dimensional pixel coordinates. The inertial transmitter can include gyroscopic and accelerometer sensors to provide six degrees of movement tracking. In one embodiment, the estimation algorithm only receives as inputs a plurality of two-dimensional pixel coordinates, a set of sensor readings generated by the gyroscopic and accelerometer sensors, and previously generated estimated motion data.

In one embodiment, the object can include at least three markers and in another embodiment, the object can include at least four markers. The object can also include a mating element for mating the object to another instrument. In yet another embodiment, the system can include at least two cameras. In one embodiment, the estimation algorithm can be or can include a Kalman filter (e.g., an Extended Kalman Filter) and/or a nonlinear observer. The inertial movement signals can be generated at a sample rate that is higher than a sample rate of the location signals generated by the camera. In one embodiment, the ratio of the sample rates can be between 3:1 and 10:1. The system can include a servo-control configured to adjust at least one of a position, a velocity, and an orientation of the object, and the servo-control can compensate for a motion disturbance detected from the estimated motion data by adjusting at least one of the position, the velocity, and the orientation of the object.

In a further aspect, a method for locating a moving object is provided that can include receiving, at a first sample rate, image data from at least one camera, said data representing at least one image of an object having a plurality of optical markers mounted thereto. The method can also include receiving, at a second higher sample rate, inertial movement signals from an inertial sensor coupled to the object and using an estimation algorithm to generate estimated motion data of the object by merging the image data and the inertial movement signals. In one embodiment, the step of using an estimation algorithm to generate estimated motion data is performed at the second sample rate. In one embodiment, the second sample rate can be at least 300 Hz. The estimated motion data can include a position of the object, a velocity of the object, and/or an orientation of the object. The estimation algorithm can operate directly on raw image data and the raw image data can comprise a plurality of two-dimensional pixel coordinates. In one embodiment, the estimation algorithm only receives as inputs a plurality of two-dimensional pixel coordinates, the inertial movement signals, and previously generated estimated motion data. The estimation algorithm can be selected from the group consisting of a Kalman filter and a nonlinear observer. In one embodiment, the method can also include actuating a servo-control to adjust at least one of a position, a velocity, and an orientation of the object in response to a disturbance detected from the estimated motion data.

In a still further aspect, a system for navigated surgery is provided that can include a surgical tool comprising a plurality of optical markers rigidly connected to the surgical tool and an inertial transmitter for transmitting high speed signals of tool movement. The system can also include at least one camera for imaging said plurality of markers and generating image data indicative of the tool location, a receiver for receiving inertial movement signals from the inertial transmitter, and a processor for executing an estimation algorithm, the estimation algorithm merging the optically-derived image data and the high speed inertial movement signals to generate estimated motion data at a frequency of at least 300 Hz.

In one embodiment, the estimated motion data can include a position of the tool, a velocity of the tool, and/or an orientation of the tool. The estimation algorithm can operate directly on raw image data and the raw image data can comprise a plurality of two-dimensional pixel coordinates. The inertial transmitter can include gyroscopic and accelerometer sensors to provide six degrees of movement tracking. In one embodiment, the estimation algorithm only receives as inputs a plurality of two-dimensional pixel coordinates, a set of sensor readings generated by the gyroscopic and accelerometer sensors, and previously generated estimated motion data. The tool can include at least three markers and in one embodiment, can include at least four markers. The system can also include at least two cameras.

The estimation algorithm can be selected from the group consisting of a Kalman filter and a nonlinear observer. The tool can also include a mating element for mating the tool to another instrument. The inertial movement signals can be generated at a sample rate that is at least three times a sample rate of the location signals generated by the camera, for example in the range of three to ten times the sample rate. The system can include a servo-control configured to adjust at least one of a position, a velocity, and an orientation of the surgical tool and the servo-control can compensate for a motion disturbance detected from the estimated motion data by adjusting at least one of the position, the velocity, and the orientation of the surgical tool.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. A number of problems with conventional methods and systems are noted in the "background" section of this application and the methods and systems disclosed herein may address one or more of these problems. By describing these problems, no admission as to their knowledge in the art is intended.

A person having ordinary skill in the art will appreciate that, although certain methods and systems are described herein with respect to navigated surgery, the scope of the present invention is not so limited. For example, the methods and devices disclosed herein can be used in any type of surgery including open and laparoscopic surgeries, and in other non-surgical applications, such as in a precision manufacturing environment, for human motion tracking (e.g., gait analysis), in virtual reality systems (e.g., for tracking a user's motion), etc.

Figure 1:
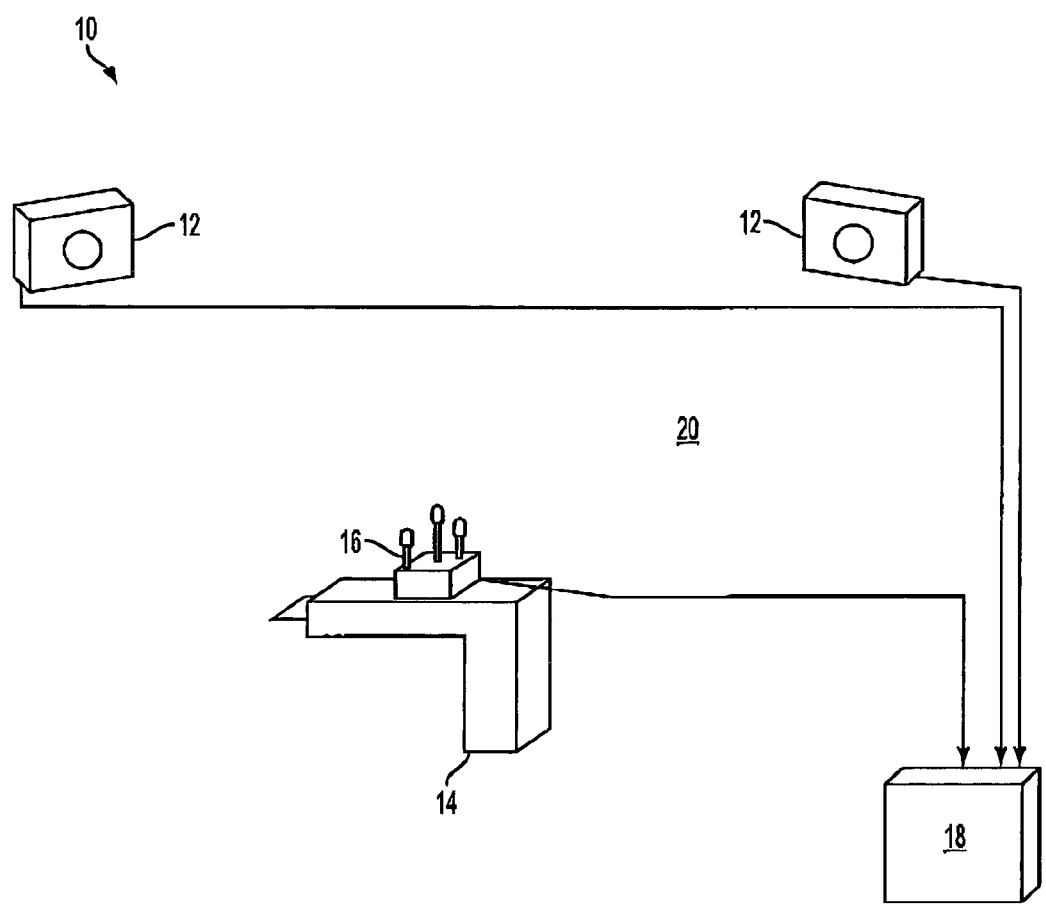
FIG. 1 is a schematic diagram of one embodiment of a system for tracking motion of an object in accordance with the present invention.

FIG. 1 illustrates one exemplary embodiment of a system for tracking motion of an object (e.g., a surgical tool). As shown, the system 10 can include a camera system 12, a sensor unit 16 coupled to an object 14, and a computer system 18. The system 10 can be installed in an operative field 20, in which various motion properties of the object 14 can be tracked and/or estimated in three-dimensional space, such as velocity, position, orientation, and the like. In one embodiment, the tracked/estimated motion properties of the object can be used to facilitate navigated surgical operations, such as by correlating the motion properties of the object 14 with one or more images of a surgical subject, patient, or site using the computer system 18. For example, the computer system 18 can be programmed to compare the measured and/or estimated motion of a surgical tool to a predetermined motion path defined with respect to an MRI or CT image of a patient's anatomy. The predetermined motion path can also be defined using data collected intra-operatively according to an image-free (or "CT-free") method. The computer system 18 can provide feedback to a surgeon or other individual operating the surgical tool, indicating whether the tool is following the predetermined motion path. The computer system 18 can also use feedback from the measured and/or estimated motion of the surgical tool to control the tool itself, for example in the case of robotic or computer/servo controlled surgical tools. These latter systems can advantageously allow for control of the surgical tool at a bandwidth superior to human reaction time, thus permitting more precise surgical procedures. Alternatively, or in addition, the methods and systems of the invention can be used with kinematic data (e.g., registration of the knee, hip, and/or ankle joint centers and/or at least one load line or leg mechanical angle(s)). For example, the surgeon can palpate landmarks on the bone surfaces using an optical tracking system. From this data, a computer system can calculate the desired motion path. Although this method makes use of cameras, it can be referred to as "image-free" because it only tracks markers attached to the patient and the tools and does not provide an image of the patient.

The camera system 12 can include one or more cameras which can each be fixed with respect to each other and with respect to the operative field 20. While as few as one camera can be used with the methods and system disclosed herein, the use of additional cameras can provide for a degree of redundancy such that the system can continue to operate if one camera fails or if a camera's line of sight to the tracked object 14 is partially or completely blocked (e.g., by a surgeon manipulating the object 14 within the operative field 20). In embodiments where more than one camera is used, the cameras can be synchronized such that they capture images at the same rate and at the same time. This can be accomplished using a variety of techniques, for example by transmitting a synchronization signal, either wirelessly or over a hardwired connection, to each of the cameras or from one camera to another.

The cameras can be or can include a variety of commercially available imaging devices (e.g., CCD-based imaging devices) capable of capturing an image of some or all of the operative field 20 through a lens system and transmitting and/or storing digital image data representative of the captured image. In one embodiment, the cameras can be capable of capturing images at a frequency of at least 60 Hz. The cameras can be communicatively coupled to the computer system 18 such that images captured by the camera system 12 can be received, stored, and/or processed on or by the computer system 18. A variety of communication mediums known in the art can be used to couple the camera system 12 to the computer system 18, as described below. The captured image data can be used to estimate the three-dimensional position, velocity, and orientation of the sensor unit 16 (and thus the object 14) with respect to the operative field 20.

Although the system is illustrated as using an optical, camera-and-marker-based, measurement system, other measurement systems known in the art can also be used, such as electromagnetic, mechanical, and/or ultrasound positioning systems.

The object 14 can be virtually any object to which the sensor unit 16 can be coupled, however in one embodiment the object 14 is a hand-held surgical tool for use in navigated surgery, such as a drill, knife, saw, catheter, guidewire, etc. The object 14 and the sensor unit 16 can optionally include mating elements to facilitate coupling therebetween. For example, the object 14 and the sensor unit 16 can include corresponding threaded interfaces, can couple together using a snap fit, friction fit, or magnetic coupling, and/or can be coupled using screws, bolts, adhesives, clamps, ties, or any other coupling device or technique known in the art. In one embodiment, the sensor unit 16 and various surgical tools can be modularly designed such that the sensor unit 16 can be easily fitted to a variety of surgical tools having different types. In another embodiment, the sensor unit 16 can be formed integrally with the object 14.

Figure 2:
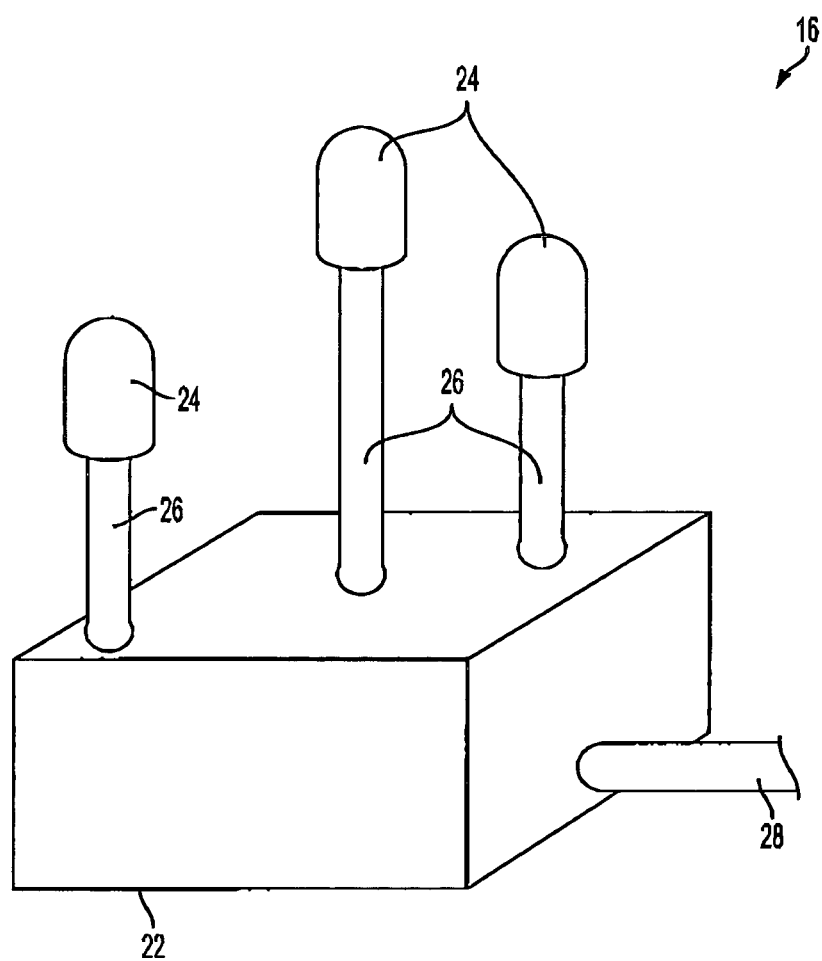
FIG. 2 is a perspective view of one embodiment of a sensor unit of the system of FIG. 1.

The sensor unit 16 can have a variety of configurations. One exemplary embodiment of a sensor unit 16 is shown in FIG. 2. As shown, the sensor unit 16 can include an inertial measuring unit (IMU) 22 and one or more markers 24 coupled to the IMU 22 via one or more connectors 26.

In the illustrated embodiment, the markers 24 are active (e.g., powered) markers in the form of light emitting diodes (LEDs), however a variety of marker types can also be employed, including for example inactive markers such as reflective markers or markers having a unique color, shape, surface pattern, etc. A person having ordinary skill in the art will appreciate that the number and position of the markers can depend on the number and position of the cameras of the camera system 12 and vice versa. For example, in an embodiment with only one camera, three or more markers can be provided to ensure optimal observability. Although the methods and systems described and illustrated herein might include or refer to a specific number of markers and/or cameras, such methods and systems are non-limiting examples and any number of markers and/or cameras can be used without departing from the scope of the present invention. Use of additional markers can advantageously provide for redundancy, for example by allowing the system to continue to operate when one or more of the markers are not visible to the camera system (e.g., when the markers are obscured by other tools, other markers, a patient, and/or a user).

The markers 24 can be positioned according to a predetermined geometry such that calculations performed on the image data generated by the camera system 12 can resolve the position and orientation of the sensor unit 16 to a desired degree of accuracy. The size and shape of the markers 24 can also be chosen to optimize the accuracy of position and orientation estimations based on the image data. In one embodiment, the geometry of the markers with respect to the sensor unit and/or the size and shape of the markers themselves can be stored in the computer system 18.

The IMU 22 can also have a variety of configurations. In one embodiment, the IMU 22 includes one or more accelerometers and one or more gyroscopes. The accelerometers and gyroscopes can be configured to periodically (e.g., at a frequency of 300-500 Hz) measure angular velocities, specific accelerations, and/or various other motion parameters and transmit such measurements to the computer system 18 or some other receiver. The frequency at which a sensor or other device takes a measurement or records data can also be referred to as the bandwidth of the sensor or device. Various commercially available accelerometers and/or gyroscopes can be used, and can be selected based on a variety of characteristics, including weight, size, accuracy, sample rate, etc. Whereas the image data captured by the camera system 12 can be generally indicative of the absolute position and orientation of the sensor unit 16, the IMU measurement data can generally indicate the dynamics of or changes in the sensor unit's 16 motion within the operative field 20.

The sensor unit can optionally include one or more leads 28 for providing power to the sensor unit 16 and/or for transmitting measurement data acquired by the IMU 22 to the computer system 18 for storage and/or processing. Alternatively, or in addition, power can be supplied to the sensor unit 16 by an internal battery and the measurement data can be transmitted wirelessly to the computer system 18, such as over a wireless TCP/IP or UDP connection.

Figure 3:
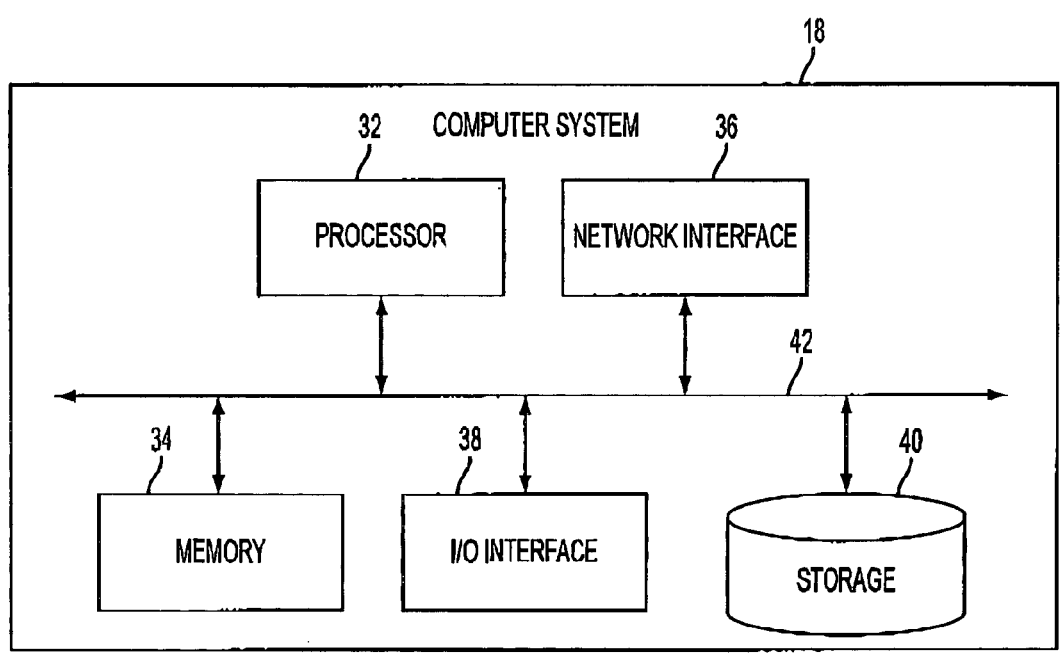
FIG. 3 is a schematic diagram of one embodiment of a computer system of the system of FIG. 1.

FIG. 3 illustrates one embodiment of a computer system 18. As shown, the computer system 18 can include one or more processors 32 which can control the operation of the computer system 18. The processor(s) 32 can include any type of microprocessor or central processing unit (CPU), including programmable general-purpose or special-purpose microprocessors and/or any one of a variety of proprietary or commercially available single or multi-processor systems, such as an Intel-based processor. The computer system 18 can also include one or more memories 34, which can provide temporary storage for code to be executed by the processor(s) 32 or for data acquired by the camera system 12 and/or the sensor unit 16. The memory 34 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 18 can be coupled to a bus system 42. The illustrated bus system 42 is an abstraction that represents any one or more separate physical busses, communication lines/interfaces, and/or multi-drop or point-to-point connections, connected by appropriate bridges, adapters, and/or controllers. The computer system 18 can also include one or more network interface(s) 36, one or more input/output (IO) interface(s) 38, and one or more storage device(s) 40.

The network interface(s) 36 can enable the computer system 18 to communicate with remote devices over a network, and can be, for example, remote desktop connection interfaces, Ethernet adapters, and/or other local area network (LAN) adapters. The IO interface(s) 38 can include one or more interface components to connect the computer system 30 with other electronic equipment (e.g., a camera system 12 and/or a sensor unit 16). For example, the IO interface(s) 38 can include high speed data ports, such as USB ports, 1394 ports, etc. Additionally, the computer system 18 can be accessible to a human user, and thus the IO interface(s) 38 can include displays, speakers, keyboards, pointing devices, and/or various other video, audio, or alphanumeric interfaces. One or more of the IO interface(s) 38 and/or the network interface(s) 36 can be a receiver for receiving sensor or image data from the IMU 22 or the camera system 12. The storage device(s) 40 can include any conventional medium for storing data in a non-volatile and/or non-transient manner. The storage device(s) 40 can thus hold data and/or instructions in a persistent state (i.e., the value is retained despite interruption of power to the computer system 18). The storage device(s) 40 can include one or more hard disk drives, flash drives, USB drives, optical drives, various media cards, and/or any combination thereof and can be directly connected to the computer system 18 or remotely connected thereto, such as over a network. The elements illustrated in FIG. 3 can be some or all of the elements of a single physical machine. In addition, not all of the illustrated elements need to be located on or in the same physical machine.

The computer system 18 can perform various processing steps on the data generated by the camera system 12 and the sensor unit 16. For example, images taken by a camera are usually distorted because of the form of the camera lens. In one embodiment, cameras with known lens distortion coefficients can be used and the distortion coefficients can be stored in the computer system 18 and used to compensate for lens distortion using a variety of techniques known in the art. The computer system 18 can also convert the raw output of the accelerometer(s) and/or gyroscope(s) of the sensor unit 16, which in one embodiment can be a voltage, into data having units more traditionally associated with motion properties. Such conversion can be performed after taking baseline sensor measurements with known inputs, or using conversion algorithms provided by the sensor manufacturer(s).

The sensor unit 16 and camera system 12 can include timing units that can be synchronized with one another using various techniques known in the art. The sensor unit 16 and/or the camera system 12 can also be configured to embed timestamp data in the sensor/image data generated thereby to facilitate accurate data fusion by the computer system 18. Alternatively, or in addition, the computer system 18 can synchronize the data generated by the camera system 12 and the sensor unit 16 to ensure that the data being merged is representative of the same point in time. For example, if it is known that there is a latency in receiving optical data from the camera system 12, the computer system 18 can align the inertial data appropriately such that the data being processed at any given "processing" time relates to the same "observation" time period. Preferably, the system 10 has a low latency such that the processing and observation times are in close proximity.

Figure 4:
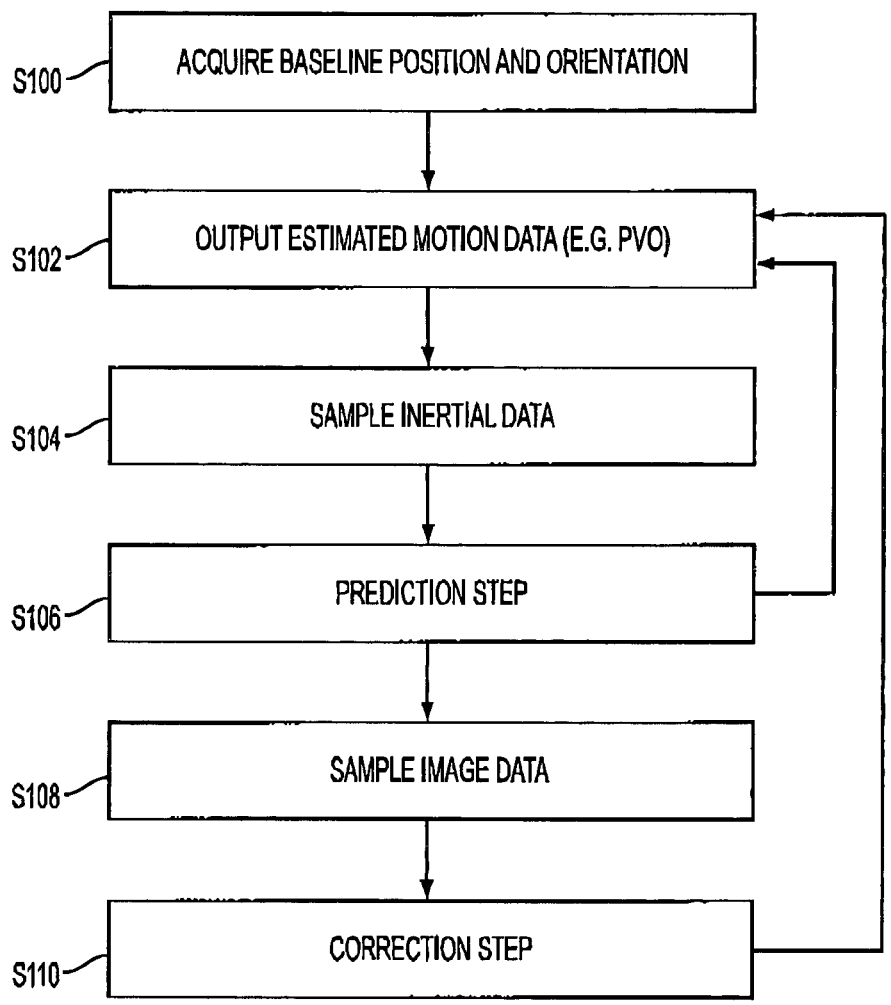
FIG. 4 is a flowchart of one embodiment of a method of using an estimation algorithm in accordance with the present invention.

FIG. 4 illustrates a flowchart of one exemplary method of using an estimation algorithm for merging the image data acquired from the camera system 12 and the inertial measurement data acquired by the sensor unit 16. While the illustrated method is discussed with respect to the system of FIG. 1, it can be implemented in or with any of the systems or embodiments disclosed herein. The processor(s) 32 of one or more computer systems 18 can be programmed to perform various steps of the method of FIG. 4, for example when a user executes a program, which can be stored on any of the storage devices 40 discussed above.

While various methods disclosed herein are shown in relation to a flowchart or flowcharts, it should be noted that any ordering of method steps implied by such flowcharts or the description thereof is not to be construed as limiting the method to performing the steps in that order. Rather, the various steps of each of the methods disclosed herein can be performed in any of a variety of sequences. In addition, as the illustrated flowchart(s) are merely exemplary embodiments, various other methods that include additional steps or include fewer steps than illustrated are also within the scope of the present invention.

As shown in FIG. 4, the method can begin at step S100 with the acquisition of a baseline position and orientation of the object to be tracked. This can be accomplished for example by acquiring a first image or set of images of the operative field 20 from the camera system 12 in the form of raw image data. Although the image data is referred to as being "raw", it can be processed (e.g., by the camera system 12 and/or the computer system 18) to correct for various factors, such as brightness, contrast, and/or the lens distortion described above. The raw image data can then be processed using a blob detection algorithm or other technique known in the art to ascertain the two-dimensional pixel coordinates of each of the markers 24 of the sensor unit 16 in the raw image data. Such processing can be implemented using hardware, software, or any combination thereof.

The coordinates of one or more landmarks in the operative field 20 can also be determined. The landmarks can be any stationary or non-stationary reference point, and in one embodiment can include stationary markers of the same type as the markers 24 of the sensor unit 16 and affixed to a surgical patient and/or a surgical table. The estimated position, velocity, and orientation of the sensor unit 16 (and thus of the object 14 coupled thereto) can thus be specified relative to the landmarks and/or relative to an origin of an operative field coordinate system. Using an estimation algorithm as explained below, the baseline position and orientation acquired in step S100 can be output as estimated motion data (e.g., as a position, a velocity, and an orientation) at step S102.

Inertial data from the IMU 22 can then be sampled at step S104 of FIG. 4. The sampled inertial data can be converted by the computer system 18 as described above. The image data acquired in step S100 (e.g., the two-dimensional pixel coordinates of the markers) and/or the inertial data sampled in step S104 can be processed in a prediction step S106 of an estimation algorithm. The estimation algorithm can estimate a state of the system (e.g., a position, a velocity, and an orientation (PVO) of the object 14) which can then be output in step S102 as estimated motion data. Again, the estimated motion data that is output can be specified as being relative to the origin of the operative field coordinate system and/or as being relative to the coordinates of one or more of the landmarks.

The inertial data can be sampled again at step S104 to update the estimated motion data. Each time the inertial data is sampled, it can be used to adjust the estimated motion data as described above with respect to the prediction step S106 of the estimation algorithm. Steps S102, S104, and S106 can be repeated any number of times before proceeding to steps S108 and S110. In one embodiment, steps S102, S104, and S106 are performed a number of times equal to the ratio of the sample rate of the IMU 22 to the sample rate of the camera system 12. In other words, if the IMU 22 can acquire inertial data at a rate of 500 Hz and the camera system 12 can acquire image data at a rate of 100 Hz, then steps S102, S104, and S106 can be repeated five times before proceeding to steps S108 and S110. An example of this timing is illustrated in FIG. 5.

Figure 5:
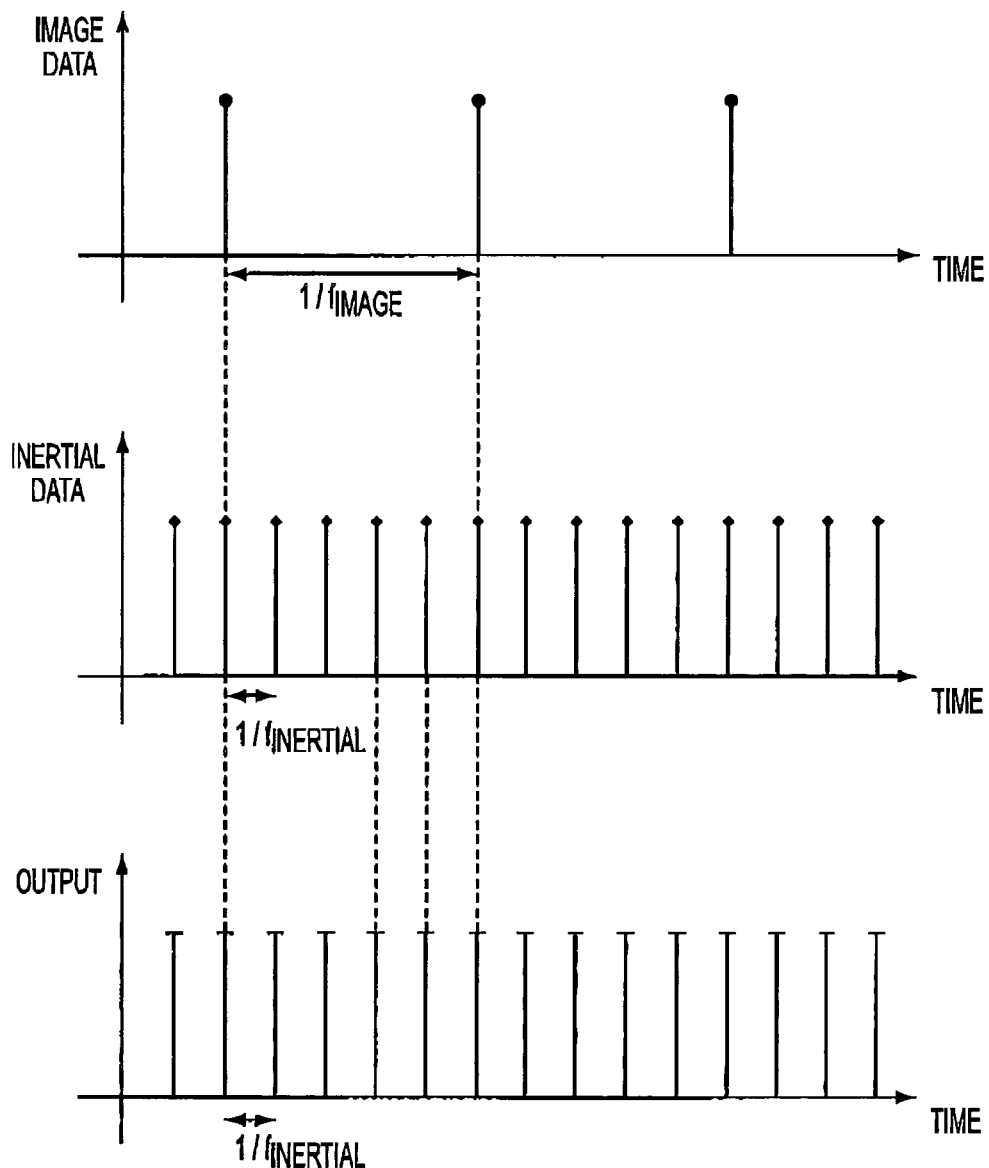
FIG. 5 is a timing diagram of one embodiment of a method of using an estimation algorithm in accordance with the present invention.

FIG. 5 shows three plots having a common time scale on the horizontal axis. The upper plot shows the rate at which image data is sampled in one embodiment of the method of FIG. 4. The middle plot shows the rate at which inertial data is sampled and the lower plot shows the rate at which the estimated motion data of the tracked object is output. As shown in the upper plot, image data can be sampled at a frequency $f_{IMAGE}$ and therefore can be sampled every $1/f_{IMAGE}$ seconds. If $f_{IMAGE}$ is 100 Hz, then image data can be sampled every 0.01 seconds. As reflected in the middle plot, inertial data can be sampled at a frequency $f_{INERTIAL}$ and therefore can be sampled every $1/f_{INERTIAL}$ seconds. If $f_{INERTIAL}$ is 500 Hz, then inertial data can be sampled every 0.002 seconds. The lower plot of FIG. 5 shows that the output rate of estimated motion data is equal to the inertial data sample rate $f_{INERTIAL}$, even though image data is only acquired at one-fifth that rate. The illustrated system can thus provide updated motion data estimations at the same rate as a purely inertial system, yet can substantially eliminate the drift and noise error typically associated therewith by periodically updating the estimated motion data with optical image data.

Referring again to FIG. 4, after steps S102, S104, and S106 have been repeated the designated number of times, the image data generated by the camera system 12 can be sampled at step S108. The sampled image data can be used, in step S110, to correct the estimated motion data from the prediction step S106, thereby correcting for any drift or noise error inherent in the sensors included in the IMU 22. After such correction is made, execution of the method of FIG. 4 can return to step S102, where the estimated motion data is again output, and then to steps S104 and S106, where the inertial data can again be sampled and the estimated motion data adjusted accordingly. Steps S102-S110 can be repeated until execution of the algorithm ceases (e.g., when a user enters a stop command into the computer system 18, for example when it is no longer necessary to track the motion of the object 14).

In some hybrid tracking systems, image data is first processed with a triangulation or back projection algorithm to determine a three-dimensional PVO of the tracked object. It is this calculated three-dimensional PVO that is input into the data fusion algorithm for merging with inertial sensor data. This preliminary calculation step can undesirably introduce latency into the tracking system, as additional processor cycles are required, for example to triangulate a position from the image data. In addition, because the underlying image data and/or the triangulation/back projection algorithm are prone to error, this error can be introduced into the data fusion algorithm and magnified thereby. In the embodiment of FIG. 4, raw image data (e.g., two-dimensional pixel coordinates of markers in a captured two-dimensional image) is input directly into the estimation algorithm, without any preliminary triangulation or back projection processing. This can advantageously reduce the overall latency and error of the tracking system.

The estimation algorithm of FIG. 4 can be or can include a Kalman Filter (e.g., an extended Kalman Filter or "EKF") and/or a nonlinear observer. An EKF is a type of recursive filter that can estimate the state of a dynamic system from a series of noisy measurements. In one embodiment, image data generated by the camera system 12 in step S108 and estimated motion data adjusted with inertial data in step S106 over a period of time can constitute a series of noisy measurements. An EKF can be applied to these measurements to estimate a state of the system 10 (e.g., a PVO of the object 14). EKFs are well known in the art and are described throughout the literature, for example in Welch and Bishop, An Introduction to the Kalman Filter, Technical Report TR 95-041 (Updated Jul. 24, 2006) University of North Carolina, Chapel Hill, N.C. 27599, the entire contents of which are incorporated herein by reference.

An estimation algorithm such as a Kalman filter or a nonlinear observer operates on the general principal that if the inputs and outputs to a system are known, and the state of the system is a function of the inputs and outputs, then the state of the system can be estimated. In other words, when the state of a system cannot be measured directly, but the inputs and outputs to the system can be so measured, the state of the system can be estimated. In the embodiment of FIG. 1, the state of the system can be represented with at least ten variables: three for the X, Y, and Z coordinates representing the position of the object 14 in the operative field 20, three for the X, Y, and Z components of the velocity of the object 14, and four for a quaternion describing the orientation of the object 14. The state of the system 10 at any given time can thus be represented as a composite state vector of these ten variables. The "inputs" to the system 10 can be represented by six variables: three for the X, Y, and Z components of the acceleration of the object 14 (as measured by the accelerometers of the IMU 22) and three for the angular velocities of the object 14 (as measured by the gyroscopes of the IMU 22). Finally, the "outputs" of the system 10 can be represented by six variables: two for each of the markers 24, representing the two-dimensional pixel coordinates of each marker (as detected in the image data generated by the camera system 12). It will be appreciated that the number of inputs will depend on the number of sensors in the IMU 22 and that the number of outputs will depend on the number of cameras in the camera system 12 and the number of markers 24. It should be noted that the "inputs" to a system are not necessarily the same as or coextensive with the "inputs" to an estimation algorithm.

In the prediction step of the estimation algorithm described above, an intermediate estimate of the system state (PVO) can be calculated using the inertial data and the previous estimated PVO. In the update/correction step of the estimation algorithm, an estimate of the system state (PVO) can be calculated using the image data and the intermediate state estimate from the prediction step. Since inertial data can be acquired at a faster rate than image data, the algorithm can include more predictions than updates.

The estimated motion data output from the estimation algorithm is generally indicative of the PVO of the individual markers 24. This estimated motion data can be processed in a data association step to find the correspondence between the marker PVOs and the three-dimensional PVO of the sensor unit 16 and object 14 with respect to the operative field 20 and/or a patient or other reference point situated therein. Since the geometry of the sensor unit 16 (and thus of the markers 24) can be known by the computer system 18, the computer system 18 can determine which imaged marker corresponds to which physical marker 24. In one embodiment, the computer system 18 can calculate the Mahalanobis distance between the markers for all possible combinations of marker associations. The computer system 18 can then either choose the combination with the smallest Mahalanobis distance (e.g., using a nearest neighbor or best-first search technique) or use a "memory" of which combination has been used at previous sample times.

With each output from the algorithm of FIG. 4, the estimated three-dimensional PVO of the object 14 can be compared by the computer system 18 to a desired three-dimensional PVO stored therein. If a discrepancy is detected, appropriate feedback can be provided (e.g., to a surgeon and/or to one or more servos controlling the movement of the object 14) to facilitate correction.

The processing algorithms and methods disclosed herein can also include various error correction or warning steps. For example, spurious camera images and/or out-of-range sensor readings can be rejected. In one embodiment, a warning can be given when it is detected that one or more of the markers is occluded in the captured image data, such that a surgeon, servo control, and/or other user can adjust the position of various objects in the operative field 20 to restore line-of-sight between the camera system 12 and the occluded marker.

Another benefit of some of the systems and methods disclosed herein is the ability to estimate a disturbance (e.g., due to a surgeon's unconscious motion error or an inhomogeneous bone structure) more quickly than in an exclusively-optical tracking system. This fast estimation of disturbances allows a servo-control or other device to correct the resulting deviation more quickly. Furthermore, the optical-inertial tracking systems disclosed herein can be configured to estimate a disturbance acting on a surgical tool, independent of the tool's geometry (e.g., without the system "knowing" the geometry of the tool).

Figure 6:
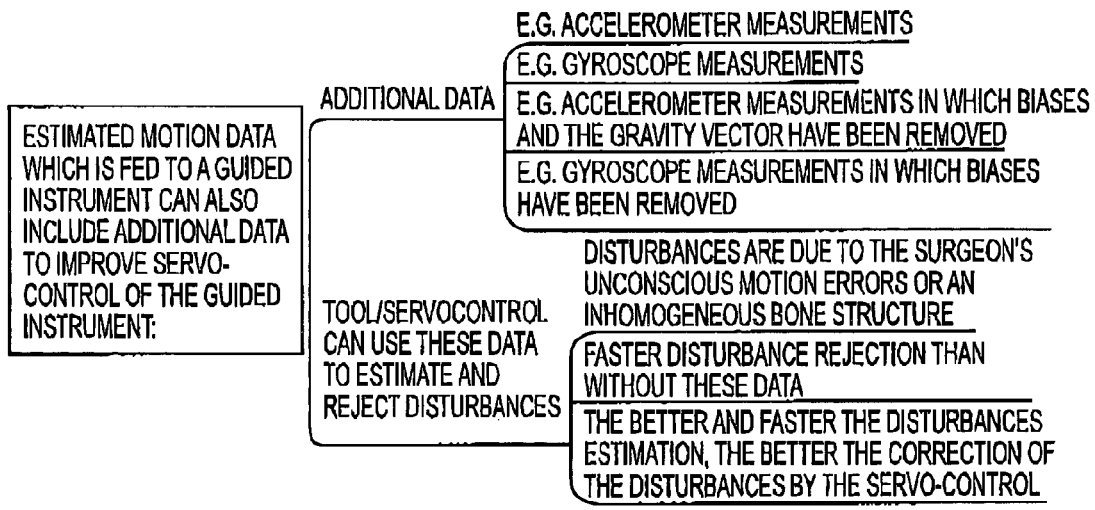
FIG. 6 is a chart illustrating one embodiment of a method of improving servo-control of a guided instrument using additional data in accordance with the present invention.

As shown in FIG. 6, estimated motion data that is fed to a guided instrument can also include additional data to improve servo-control of the guided instrument. Such additional data can include, for example, accelerometer measurements, gyroscope measurements, accelerometer measurements in which biases and the gravity vector have been removed, gyroscope measurements in which biases have been removed, etc. This additional data can be used by the tool and/or a servo control to estimate and reject disturbances (e.g., disturbances due to a surgeon's unconscious motion errors or an inhomogeneous bone structure). This allows for faster disturbance detection than is otherwise possible without such additional data. By improving the speed of disturbance detection, the servo control is better able to correct the disturbances.

Many computer-assisted surgery systems use an image-free tracking system to acquire patient data intra-operatively. These are also called optical tracking systems and consist of two or more infrared cameras and markers which are fixed to the patient and tools. In orthopedic surgery systems, e.g., for knee replacement, the system acquires relevant patient anatomical landmarks and calculates appropriate prosthesis placement based on built up frame of reference. It then defines the desired cutting planes for the knee implant.

Cutting jigs are fixed to the patient's bone in accordance with the desired cutting planes. They guide the bone saw or other tool mechanically with good accuracy, but mounting the jigs takes time and they have to be pinned to the bone. Using a handheld saw without any cutting jigs can have several advantages: the procedure can be less invasive, demand less surgical material in the OR, and save time. However, such systems need to produce cuts with the same or even better accuracy to be a valuable improvement.

While a robotic system can conceivably achieve this task of cutting along a desired path, many surgeons wish to keep control over the cutting procedure. Therefore, an intelligent handheld tool is provided herein which combines the surgeon's skills with the accuracy, precision, and speed of a computer-controlled system. The tool can be small and lightweight so as not to impede on the surgeon's work, compatible with existing computer-assisted surgery systems, and relatively low-cost.

Controlling the tool position and keeping it along the desired cutting path can necessitate some or all of the following steps: (1) define desired cutting plane relative to the patient, (2) track tool position and orientation relative to the patient, and (3) compare desired and actual positions and correct the tool position accordingly. The first step can be performed by the surgery system and the second by a tracking system. The handheld tool can optionally be configured to carry out the third step.

The handheld tool provided herein can be an extension for an image-free or image-based computer-assisted surgery system, and thus can make use of an optical tracking system. The tool can be servo-controlled with motors which can change the position of a blade or other working component of the tool. While embodiments are disclosed herein using a saw as an example, the systems and methods disclosed have application to drilling tools, pinning tool, burring tools, and various other tools.

Since a surgeon has a reaction time of about $\frac{1}{100}$ s (which corresponds to a frequency of 100 Hz), the tools disclosed herein can be configured to react faster so as to be able to correct motion errors. This demands a fast tracking system (e.g., a tracking system with a bandwidth of at least about 100

Hz, and preferably at least about 200 Hz, and more preferably at least about 300 Hz. Optical tracking, with its maximal bandwidth of 60 Hz, is not suitable.

In one embodiment, the handheld tool can autonomously change the position of its tip (i.e., of its blade or other working component) with the help of servo-motors which control the motion of the tip relative to the tool. This technique can be called servo-control and can be used to correct small deviations from the desired position. In the case of a handheld surgery tool, such deviations could be due to the surgeon's unconscious motion errors or an inhomogeneous bone structure. The action of the servo-motors is determined by the error between the actual and the desired position, the latter of which can be defined by the surgery system. The actual position can be provided by a tracking system. The servo-control compares the desired and actual path and actuates the motors accordingly. Tracking systems having a high bandwidth and a low latency can improve the performance of the servo-control.

The discussion that follows details one exemplary simulation of this principle for a very simple model whose motion is constrained to a single axis. In the simulation, a high-bandwidth optical-inertial tracking system using an Extended Kalman Filter is used to fuse sensor data. A test with an experimental setup showed that optical-inertial systems do indeed follow motion faster than an optical tracking system with a low bandwidth.

Figure 7:
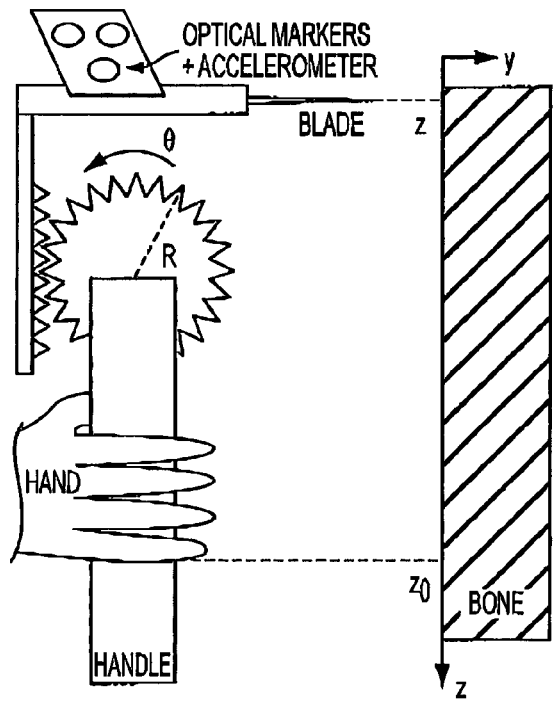
FIG. 7 is a schematic diagram of one embodiment of a computer-assisted surgery system in accordance with the present invention.

The tool used in the simulation is illustrated in FIG. 7 and comprises a handle and a blade connected by a gearing mechanism which is actuated by a motor. For purposes of the simulation, the surgical goal is to cut in y direction at a desired position $z_r$. The surgeon moves the tool in y direction at a speed of 0.5 cm/s. A deviation from the desired $z_r$ due to a change of bone structure is modeled by a disturbance D acting along z. In this simple model it is assumed that the tool's motion is constrained along z.

The blade position z is determined by $z=R\theta+z_0$ and $m\ddot{z}=F+D+mg$ where R is the ray of the gear wheel, $\theta$ the wheel's angular position, $z_0$ the handle's position, F the force applied by the gear, m the mass of the subsystem carrying the blade and g is gravity. The motor is governed by $J\ddot{\theta}=U-RF$ where J is the motor and gear inertia and U the control input. Combining these equations gives:

$$\ddot{z} = \underbrace{\frac{U}{mR+J/R}}_{u} + \underbrace{\frac{D}{m+J/R^2} + \frac{\ddot{z}_0-g}{1+mR^2/J}}_{d} + g \quad (0.1)$$

This yields the simplified system $\dot{z}=v$, $\dot{v}=u+d+g$. d includes the disturbance D due to bone structure as well as disturbances due to the surgeon motion (modeled by $\ddot{z}_0$). An optical tracking system measures the position $z_m=z$ with a frequency of $1/T=50$ Hz at discrete instants $z_{m,k}=z_m(kT)$, an inertial sensor (accelerometer) measures $a_m=u+d+a_b$ where $a_b$ is the accelerometer constant bias. The inertial measurements are considered continuous because their frequency is much higher than that of the optical ones. The simulation is based on three systems using different types of measurements in a standard servo-control design. Measurement noise is not taken into account in the simulation. In all cases h, L, and K are appropriately calculated constant gains and d is modeled as a constant.

A first system uses only optical measurements $z_{m,k}$. An observer estimates the state $x=[z, v, d+g]^T$:

$$\text{prediction: } \dot{\hat{x}}^- = \begin{bmatrix} \hat{v} \\ u+\widehat{d+g} \\ 0 \end{bmatrix} = \begin{bmatrix} 0 & 1 & 0 \\ 0 & 0 & 1 \\ 0 & 0 & 0 \end{bmatrix}\hat{x}^- + \begin{bmatrix} 0 \\ 1 \\ 0 \end{bmatrix}(u) \quad (0.2)$$

$$\text{correction: } \hat{x}_k = \hat{x}_k^- + L(z_{m,k-1} - \hat{z}_{k-1}) \quad (0.3)$$

where $\hat{x}_k^- = \int_{kT-T}^{kT}\dot{\hat{x}}^-(\tau)d\tau$ with $\hat{x}^-(kT-T)=\hat{x}_{k-1}$. The controller reads $u_k=-K\hat{x}+hz_r$. This first system corresponds to the case where only an optical tracking system is used.

A second system uses both optical and inertial data, e.g., as described above. A first observer with state $x=[z, v, a_b-g]^T$, measured input $a_m$, and discrete visual measurements $z_{m,k}$ reads:

$$\text{prediction: } \dot{\hat{x}}^- = [\hat{v}, a_m - \widehat{a_b-g}, 0]^T \quad (0.4)$$

$$\text{correction: } \hat{x}_k = \hat{x}_k^- + L(z_{m,k-1} - \hat{z}_{k-1}) \quad (0.5)$$

where $\hat{x}_k^- = \int_{kT-T}^{kT}\dot{\hat{x}}^-(kT-T)=\hat{x}_{k-1}$. This observer gives a continuous estimation $\hat{z}(t)$ which is used as a measurement $z_m(t)$ for a second observer with state $\tilde{x}=[\tilde{z}, \tilde{v}, \tilde{d}+g]^T$:

$$\dot{\tilde{x}}(t) = [\tilde{v}, \widetilde{d+g}+u, 0]^T + L(z_m(t)-\hat{z}(t)) \quad (0.6)$$

The controller equation is $u=-K\hat{\tilde{x}}+hz_r$.

A third system uses optical and inertial data and includes tracking and control that are more tightly coupled than in the second system. A first observer is used to estimate the disturbance d with inertial measurements $a_m=u+d+a_b$:

$$\widehat{\dot{d}+a_b} = l(a_m-u-\widehat{d+a_b}) \quad (0.7)$$

This observer gives a continuous estimation $\widehat{d+a_b}(t)$ which is used as input for the second controller-observer. Its state is $x=[z, v, a_b-g]^T$ and it uses discrete visual measurements $z_{m,k}$:

$$\text{prediction: } \dot{\hat{x}}^- = [\hat{v}, u+\widehat{d+a_b}-\widehat{a_b-g}, 0]^T \quad (0.8)$$

$$\text{correction: } \hat{x}_k = \hat{x}_k^- + L(z_{m,k-1} - \hat{z}_{k-1}) \quad (0.9)$$

where $\hat{x}_k^- = \int_{kT-T}^{kT}\dot{\hat{x}}^-(\tau)d\tau$ with $\hat{x}^-(kT-T)=\hat{x}_{k-1}$. The control input is $u_k=-K\hat{x}_k+hz_r-\widehat{d+a_b}$.

Figure 8:
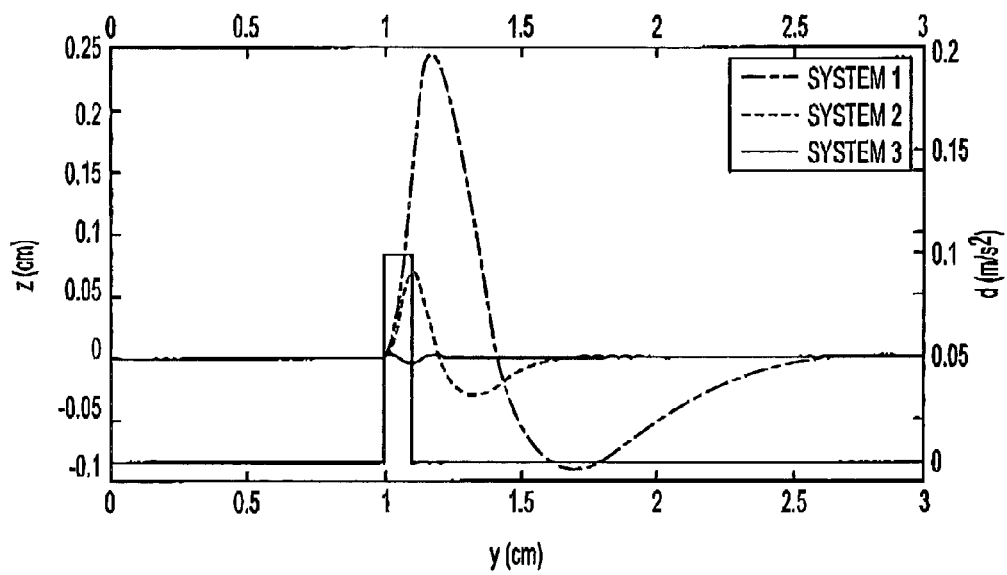
FIG. 8 illustrates the results of a simulation that compared the response time of an optical tracking system to the response time of one embodiment of an optical-inertial tracking system in accordance with the present invention.

FIG. 8 shows simulated cuts for these three systems for a desired cutting position $z_r=0$ cm and a disturbance d occurring from t=2.002 s and t=2.202 s. As shown, the disturbance causes the largest and longest deviation in the first system (shown as "system 1"). In the second system (shown as "system 2"), the position deviation can be corrected much faster and its amplitude is much smaller. Using the third system (shown as "system 3") can correct the deviation even better. This simulation shows that using inertial sensors with a higher bandwidth allows the servo-control to correct a deviation caused by a disturbance much better than a system with a low bandwidth such as an optical tracking system.

It is important to note that the controller-observer for the first system cannot be tuned to reject the disturbance faster, since the choice of K and L is constrained by the frequency of the optical measurements.

This simple model of the handheld tool shows the differences between three servo-control strategies in a concise manner. It will be appreciated that the principles and concepts illustrated by this simple model also have application in more complex systems.

In one embodiment of an optical-inertial tracking system, motion is tracked using a stationary stereo camera pair and a sensor unit. The sensor unit comprises an inertial measuring unit (IMU) and three optical markers and is attached to a handheld tool. The tracking system can be used to calculate the position and orientation of the sensor unit relative to the cameras. This is achieved by a data fusion algorithm using a model of the system and the data from the cameras and the IMU. The model and the data fusion algorithm for this embodiment are discussed below.

Mathematical Model

Coordinate Systems: The motion of the sensor unit can be expressed in camera coordinates which are denoted by C and are fixed to the right camera center. Their unit vectors are $E_1=[1,0,0]^T$, $E_2=[0,1,0]^T$ and $E_3=[0,0,1]^T$. The camera's optical axis runs along $E_1$. Image coordinates are expressed in the image sensor coordinate system S which is attached to one of the corners of the camera's image sensor. The left camera coordinate system is denoted by CL and the image sensor coordinate system by SL. The left camera unit vectors are $\tilde{E}_1$, $\tilde{E}_2$, and $\tilde{E}_3$. Coordinates C and CL are related by a constant transformation. The body coordinates, denoted by B, are fixed to the origin of the IMU frame and are moving relative to the camera frames. The world coordinate system is Earth-fixed and denoted by W.

Dynamics and Output Model: The following state variables are used in the model for this embodiment: sensor unit position $C_p$, velocity $C_v$ and quaternion $BC_q$ (representing orientation), accelerometer bias $^B a_b$ and gyroscope bias $^B \omega_b$. The dynamics equations read:

$$^C\dot{p} = {}^C v, \quad {}^C\dot{v} = {}^C G + {}^{BC}q*(a_m - v_a - {}^B a_b)*{}^{BC}q^{-1}, \qquad (0.10)$$

$$^{BC}\dot{q} = \frac{1}{2}{}^{BC}q*(\omega_m - v_\omega - {}^B \omega_b), \quad {}^B\dot{a}_b = v_{ab}, \quad {}^B\dot{\omega}_b = v_{\omega b}$$

where $^C G = {}^{WC}q*{}^W G*{}^{WC}q^{-1}$ is the gravity vector expressed in camera coordinates. $^W G=[0, 0, g]^T$ is the gravity vector in the world frame with g=9.81 m/s² and $^{WC}q$ describes the (constant) rotation from world to camera coordinates. Quaternion multiplication is denoted by "*". $^B a_m$ and $^B \omega_m$ are the sensor unit measured accelerations and angular velocities which are considered as the system's inputs. They are corrupted by noises $v_a$ and $v_\omega$ and have unknown constant biases $^B a_b$ and $^B \omega_b$.

The outputs are the marker images. A standard pinhole model is used in this embodiment to project the marker positions to the cameras. Further details on such a technique are provided in Hartley, R., Zisserman, A.: Multiple View Geometry in Computer Vision. Cambridge University Press, 2nd edn. (2003), the entire contents of which are incorporated herein by reference. The measured output for the right camera for the ith marker (with i=1, . . . , l where l is the number of markers) reads $$y_{im} = {}^S y_i + \eta_{yi} = \frac{f_R}{\langle {}^C m_i, {}^C E_1\rangle}\begin{bmatrix}\langle {}^C m_i, {}^C E_2\rangle \\ \langle {}^C m_i, {}^C E_3\rangle\end{bmatrix} + {}^S u_R + \eta_{yi} \qquad (0.11)$$

where $f_R$ is the focal distance and $^S u_R$ is the principal point of the right camera. <a, b> denotes the scalar product of vectors a and b. The measurement is corrupted by noise $\eta_{yi}$. The position of marker i is calculated according to $^C m_i = {}^C p + {}^{BC}q*{}^B m_i*{}^{BC}q^{-1}$ using the known marker position $^B m_i$ in body coordinates.

The output for the left camera reads:

$$y_{(i+l)m} = {}^{SL}y_i + \eta_{y(i+l)} \qquad (0.12)$$
$$= \frac{f_L}{\langle {}^{CL}m_i, {}^{CL}\tilde{E}_1\rangle}\begin{bmatrix}\langle {}^{CL}m_i, {}^{CL}\tilde{E}_2\rangle \\ \langle {}^{CL}m_i, {}^{CL}\tilde{E}_3\rangle\end{bmatrix} + {}^{SL}u_L + \eta_{y(i+l)}$$

where subscript L refers to the left camera. The marker position $^{CL}m_i$ is calculated using the constant transformation between left and right camera coordinates:

$$^{CL}m_i = R_{St}{}^C m_i + t_{St}.$$

Data Fusion Algorithm

In this embodiment, an extended Kalman filter (EKF) is used to fuse inertial and optical data and obtain an estimation of the sensor unit position and orientation. Since a quaternion is to be estimated, the standard EKF is modified to preserve the unit norm. For the quaternion, the correction term $\hat{q}K_q(y-h(\hat{x}, u))$ and an error quaternion $e_q = \hat{q}^{-1}*q$ are used. This gives the so-called Multiplicative EKF (MEKF) which preserves the quaternion unit norm. Further details on EKFs can be found in Crassidis, J. L., Markley, F. L., Cheng, Y.: Survey of nonlinear attitude estimation methods. J Guid Control Dynam 30(1), 12-28 (2007), the entire contents of which are incorporated herein by reference. The MEKF for this embodiment (0.10)-(0.12) reads:

$$^C\dot{\hat{p}} = {}^C\hat{v} + K_p E, \qquad (0.13)$$
$$^C\dot{\hat{v}} = {}^C G + {}^{BC}\hat{q}*(a_m - {}^B\hat{a}_b)*{}^{BC}\hat{q}^{-1} + K_v E,$$
$$^{BC}\dot{\hat{q}} = \frac{1}{2}{}^{BC}\hat{q}*(\omega_m - {}^B\hat{\omega}_b) + K_q E * {}^{BC}\hat{q},$$
$$^B\dot{\hat{a}}_b = K_a E, \quad {}^B\dot{\hat{\omega}}_b = K_\omega E$$

with output error $E = y_m - \hat{y}$. The state error is considered: $e_p = \hat{p} - p$, $e_v = \hat{v} - v$, $e_q = {}^{BC}\hat{q}^{-1}*{}^{BC}q$, $e_a = \hat{a}_b - a_b$ and $e_\omega = \hat{\omega}_b - \omega_b$. Also so, the corresponding error system is linearized around $\bar{e} = (\bar{e}_p, \bar{e}_v, \bar{e}_q, \bar{e}_a, \bar{e}_\omega) = (0,0,1,0,0)$. The linearized error system satisfies:

$$\Delta\dot{e} = (A - KC)\Delta e - Mv + KN\eta \qquad (0.14)$$

up to higher order terms where $K=[K_p, K_v, K_q, K_a, K_\omega]$, $v=[v_a, v_\omega, v_{ab}, v_{\omega b}]$, $\eta = \eta_y$, and A, C, M and N depend on the estimated state. This permits the gain K to be calculated as in a standard extended Kalman filter: $K=PC^T R^{-1}$ where P satisfies $\dot{P} = AP + PA^T + Q - PC^T R^{-1} CP$. $Q = M\tilde{Q}M^T$ and $R = N\tilde{R}N^T$ where $\tilde{Q}$ and $\tilde{R}$ contain sensor noise intensities.

In this embodiment, the choice of the output in the system model and in the MEKF advantageously improves the latency of the system's fusing of optical and inertial data. This is because, as explained above, the system operates on raw image data. Other systems use marker positions $^C m_i$ which have been calculated by an optical tracking system as output measurements. Since pose estimation from optical data demands complex computations, this produces an unacceptable latency in the measurements. The present embodiment reduces this latency.

Experimental Setup and Results

An experimental setup was prepared using an ADIS16355 IMU (available from Analog Devices, Inc. of Norwood, Mass.) and three infrared LEDs. The setup also included a stereo camera system comprising two Wiimote image sensors (available from Nintendo of America of Redmond, Wash.)

fixed in a stereo camera rig. The image sensors were desoldered from the Wiimote such that they could be used independently therefrom. Further details on this technique can be found in Jürss, U., Rudolph, W.: Tracking hot spots. elektor 383 (11 2008), the entire contents of which are incorporated herein by reference. These image sensors "see" up to four luminous points and output the point coordinates via an I2C protocol. Data from both sensors were acquired by an Atmega2560 microcontroller (available from Atmel Corporation of San Jose, Calif.). The sensor readings were synchronized with a camera sample rate of 16.7 Hz and an IMU sample rate of 250 Hz and the data were sent to a PC serial port. The data was processed offline with Matlab/Simulink (available from The MathWorks, Inc. of Natick, Mass.).

The sensor unit was set on a horizontal surface at a distance of about 1m from the stereo camera rig. It was then moved quickly by hand mainly along the y axis. This experiment represents a small unintentional motion of a surgeon holding a handheld tool.

The experimental data was fed to the MEKF which estimated the sensor unit position and orientation. To evaluate the results and compare them to optical tracking, only optical data from the same set was used to calculate the pose, following the methods described in Hartley, R., Zisserman, A.: Multiple View Geometry in Computer Vision. Cambridge University Press, 2nd edn. (2003), the entire contents of which are incorporated herein by reference, and in Umeyama, S.: Least-squares estimation of transformation parameters between two point patterns. IEEE T Pattern Anal 13(4), 376-380 (1991), the entire contents of which are incorporated herein by reference.

Figure 9:
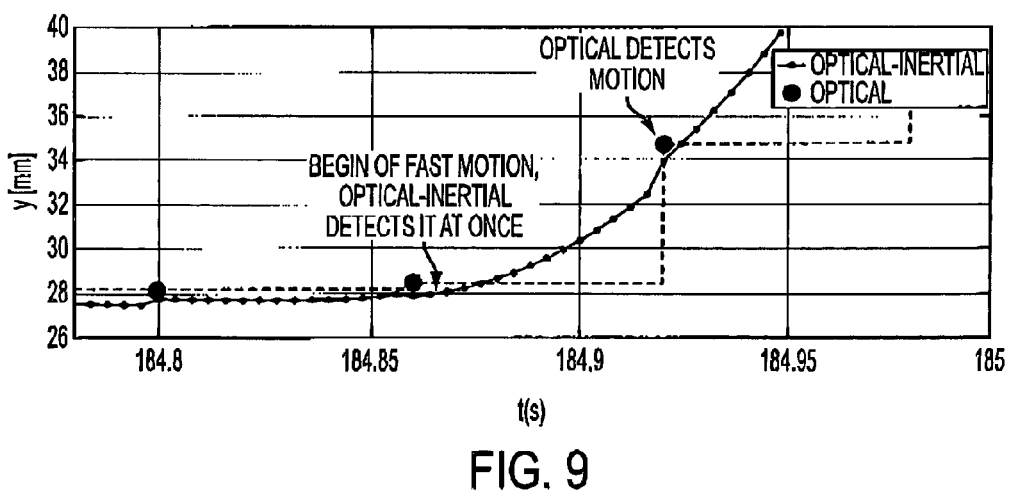
FIG. 9 illustrates the results of an experiment that compared the response time of an optical tracking system to the response time of one embodiment of an optical-inertial tracking system in accordance with the present invention.

FIG. 9 shows the experimental results. The dashed line shows the y coordinate of the estimated position for the optical tracking system. The solid line shows the y coordinate of the estimated position for the optical-inertial tracking system. Each circle on a line indicates a new estimated value. As shown, optical tracking alone detects the motion much later than the optical-inertial system. This is in accordance with the simulation discussed above in which the second system estimated the disturbance faster than the first system.

Further understanding of various aspects of the systems and methods disclosed herein can be obtained by reference to the following discussion regarding observers and data fusion, which describes one or more non-limiting exemplary embodiments of such systems and methods.

Observer 1.1 Representation of a Dynamic System

A dynamic system can be represented by a mathematical model. For this model, there is defined a state x, an input u, and an output y. x, u, and y are time-varying signals and can be vectors.

The system dynamics are represented by a differential equation:

$$\dot{x}=f(x, u) \text{tm} \quad (1.1)$$

where $\dot{x}$ is the derivative of x with respect to time and f is a function.

The output is governed by the following equation:

$$y=h(x, u) \quad (1.2)$$

where h is a function.

This is the (time–) continuous representation. The discrete representation is as follows:

$$x_k=f_d(x_{k-1}, u_k) \quad (1.3)$$

$$y_k=h_d(x_k, u_k) \quad (1.4)$$

where $f_d$ and $h_d$ are functions and k is a time index.

The input and the output are assumed to be known (y is measured and u is measured or known as a control input). The system state is not known.

1.2 Observer for a Dynamic System

An observer estimates the unknown signal x from the known signals u and y. The estimated state is denoted $\hat{x}$.

Figure 10:
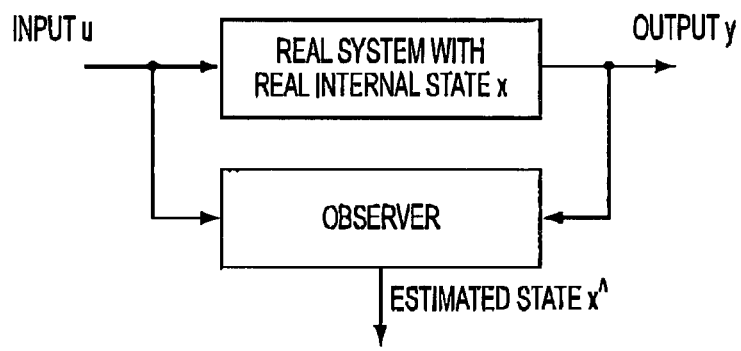
FIG. 10 is a schematic illustration of the relation between a real system and an observer in one embodiment of an object tracking system according to the present invention.

FIG. 10 shows the relation between the real system and the observer. Regarding the observer, its "input" are the system's input and output and its "output" is the estimated state.

1.3 Mathematical Description of an Observer

A very general observer is the following set of equations:

$$\dot{z}=F(z, u, y) \quad (1.5)$$

$$\hat{x}=G(z) \quad (1.6)$$

which satisfy the following two conditions:

1. if $y=h(\hat{x},u)$, then $(\hat{x}(t), u(t))$ is a solution of the model (1.1).

This means that the following equation has to hold true:

$$\dot{\hat{x}} = \frac{\partial G}{\partial z}(z) \cdot F(z, u, h(\hat{x}, u)) = f(\hat{x}, u) \quad (1.7)$$

where $$\frac{\partial G}{\partial z}(z)$$

is the partial derivative of G(z) with respect to z

2. $\hat{x} \to x$ as $t \to \infty$

Up to a (local) change of coordinates equation (1.5) can be expressed in the following form:

$$\dot{\hat{x}}= \mathcal{F}(\hat{x}, P, u, y) \quad (1.8)$$

$$\dot{P}= \mathcal{G}(\hat{x}, P, u, y) \quad (1.9)$$

where the sum of the dimensions of $\hat{x}$ and P equals the dimension of z.

Thanks to condition 1 of the general observer, equation (1.8) can be rewritten locally as:

$$\dot{\hat{x}}=f(\hat{x}, u)+g(\hat{x},P, u, y) \quad (1.10)$$

where $g(\hat{x},P, u, h(\hat{x}, u))=0$ for all $\hat{x}$, u, and P.

Equation (1.9) can be developed locally to give $$\dot{P}= \mathcal{G}_1(\hat{x}, P, u)+ \mathcal{G}_2(\hat{x}, P, u, y) \quad (1.11)$$

Considering the observer as expressed in equations (1.10)-(1.11), it can be seen as a copy of the system (more precisely of the system's model), $\dot{\hat{x}}=f(\hat{x}, u)$, to which a "correcting" term g ($\hat{x}$, P, u, y) is added, which depends on a parameter P and output y. The expression for P can be split into two terms of which only one depends on y.

An observer can be implemented in three different forms: continuous, continuous-discrete, or discrete. These distinctions have to be made because measurements are always discrete but the system model is usually continuous. They are described in sections 1.3.1, 1.3.2, and 1.3.3 below. Continuous-discrete and discrete observers can be implemented in two forms: single-rate or multi-rate, depending on the sample rates of the input and output measurements. These two forms are presented below in sections 1.3.4 and 1.3.5, respectively.

1.3.1 Continuous Form

The system model is continuous and the measurements (input and output) are considered to be continuous as well. The solutions of equations (1.10) and (1.11) are calculated to give the estimation $\hat{x}$.

1.3.2 Continuous-discrete Form

The system model is continuous and the input measurements are considered to be continuous as well. The output measurements are discrete with the sample rate h. Equation (1.10) can be split into two terms and the calculation of $\hat{x}$ into two steps. The same is true for (1.11) and the calculation of P. These two steps are called prediction and correction. The prediction step continuously calculates the solution of the equation:

$$\dot{\hat{x}}(t) = f(\hat{x}(t), u(t)) \quad (1.12)$$

using input u(t) and the previous estimate $\hat{x}_{k-1}^{corr}$ as initial condition $\hat{x}((k-1)h)$. This gives the discrete "predicted" value $\hat{x}_k^{pred} := \hat{x}(kh)$. This step also continuously calculates the solution of the equation:

$$\dot{P}(t) = \mathscr{G}_1(\hat{x}(t), P(t), u(t)) \quad (1.13)$$

using input u(t) and the previous estimates $\hat{x}_{k-1}^{corr}$ and $P_{k-1}^{corr}$ as initial conditions $\hat{x}((k-1)h)$ and $P((k-1)h)$. This gives the discrete "predicted" value $P_k^{pred} := P(kh)$. The correction step uses the predicted state $\hat{x}_k^{pred}$ and "corrects" it according to the output measurement:

$$\hat{x}_k^{corr} = m_d(\hat{x}_k^{pred}, P_k^{pred}, u_k, y_k) \quad (1.14)$$

where $m_d$ and is a function.

$P_k^{pred}$ is then updated to give $P_k^{corr}$.

Both $\hat{x}_k^{pred}$ and $\hat{x}_k^{corr}$ can be considered as the state estimate $\hat{x}_k$. This depends on the timing of the prediction and correction steps. The same applies to $P_k$, $P_k^{pred}$ and $P_k^{corr}$, as detailed below in sections 1.3.4 and 1.3.5.

1.3.3 Discrete Form

The system model is discrete (equations (1.1-1.2) and all of the measurements are as well. The prediction step calculates the discrete "predicted" value $\hat{x}_k^{pred}$, using the model equation (1.3), the previous estimate $\hat{x}_{k-1}$ and input $u_k$:

$$\hat{x}_k^{pred} = f_d(\hat{x}_{k-1}, u_k) \quad (1.15)$$

$P_k^{pred}$ is calculated using $P_{k-1}$.

The correction step is the same as in the continuous-discrete form.

Both $\hat{x}_k^{pred}$ and $\hat{x}_k^{corr}$ can be considered as the state estimate $\hat{x}_k$. This depends on the timing of the prediction and correction steps. The same applies to $P_k$, $P_k^{pred}$ and $P_k^{corr}$, as detailed below in sections 1.3.4 and 1.3.5.

1.3.4 Single-rate Form

In the single-rate form, the input and output signals have the same sample rate. Prediction and correction steps are executed at this single rate. A prediction step is being followed immediately by a correction step. The prediction step at time instant k uses $\hat{x}_{k-1}^{corr}$ and $P_{k-1}^{corr}$ initialization. The correction step following immediately afterwards (also at time instant k) uses $\hat{x}_k^{pred}$ and $P_k^{pred}$, as described in the equation (1.14). The observer's output is $\hat{x}_k = \hat{x}_k^{corr}$. The following equations show two filter cycles, each consisting of a prediction and a correction:

$$\text{cycle 1} = \begin{cases} \hat{x}_k^{pred} = f_d(\hat{x}_{k-1}^{corr}, u_k) \\ \hat{x}_k^{corr} = m_d(\hat{x}_k^{pred}, P_k^{pred}, u_k, y_k) \end{cases} \quad (1.16)$$

$$\text{cycle 2} = \begin{cases} \hat{x}_{k+1}^{pred} = f_d(\hat{x}_k^{corr}, u_{k+1}) \\ \hat{x}_{k+1}^{corr} = m_d(\hat{x}_{k+1}^{pred}, P_{k+1}^{pred}, u_{k+1}, y_{k+1}) \end{cases} \quad (1.17)$$

1.3.5 Multi-rate Form

In the multi-rate form, the input and output signals have different sample rates. Considered here is the case when the input sample rate is higher than the output sample rate. Also, this description is restricted to the case where the output sample rate is an integer multiple of the input sample rate. Consequently, whenever an output measurement is made, a new input value is available, too.

Prediction steps are executed at the input sample rate, that is every time a new input value is available. The prediction step uses the observer output $\hat{x}_{k-1}$ from the previous step which can be a prediction or a correction, depending on the timing, as initialization. The observer's output is $\hat{x}_k = \hat{x}_k^{pred}$ at each prediction step, except for the prediction steps which are immediately followed by a correction.

Correction steps are executed at the output sample rate, that is every time a new output value is available. Since the input sample rate is higher than the output sample rate, there are more predictions than corrections and a correction is always preceded by a prediction. Hence, the correction uses $\hat{x}_k^{pred}$ and $P_k^{pred}$. The observer's output is $\hat{x}_k = \hat{x}_k^{corr}$ at each correction step.

The following equations show a sequence of predictions and corrections as an example for a multi-rate observer in discrete form.

$$\text{prediction + correction} \begin{cases} \hat{x}_k^{pred} = f_d(\hat{x}_{k-1}^{pred}; u_k) \\ \hat{x}_k^{corr} = m_d(\hat{x}_k^{pred}, P_k^{pred}, u_k, y_k) \end{cases} \quad (1.18)$$

$$\text{prediction} \{ \hat{x}_{k+1}^{pred} = f_d(\hat{x}_k^{pred}, u_{k+1}) \quad (1.19)$$

$$\text{prediction} \{ \hat{x}_{k+2}^{pred} = f_d(\hat{x}_{k+1}^{pred}, u_{k+2}) \quad (1.20)$$

$$\text{prediction} \{ \hat{x}_{k+3}^{pred} = f_d(\hat{x}_{k+2}^{pred}, u_{k+3}) \quad (1.21)$$

$$\text{prediction} \{ \hat{x}_{k+4}^{pred} = f_d(\hat{x}_{k+3}^{pred}, u_{k+4}) \quad (1.22)$$

$$\text{prediction + correction} \begin{cases} \hat{x}_{k+5}^{pred} = f_d(\hat{x}_{k+4}^{pred}; u_{k+5}) \\ \hat{x}_{k+5}^{corr} = m_d(\hat{x}_{k+5}^{pred}, P_{k+5}^{pred}, u_{k+5}, y_{k+5}) \end{cases} \quad (1.23)$$

A correction step is followed by five predictions and another correction.

1.4 Observer Types

Different types of observers exist which all are essentially of the form of the general observer (1.5)-(1.6). Discrete or continuous-discrete implementations as described in sections 1.3.2 and 1.3.3 always contain a prediction and a correction (sometimes called "update") step.

The Extended Kalman Filter is one well-known example of an observer. It is presented in section 1.6.

1.5 Observer Applications

Observers can be used for data fusion applications where data from multiple sources is combined to calculate the internal state of a system. Section 1.7 introduces observers for data fusion and section 2 gives details on the data fusion from optical and inertial data.

1.6 Extended Kalman Filter

The Extended Kalman Filter, which is described further in Mohinger S. Grewal, Lawrence R. Weill, and Angus P.

Andrews. *Global positioning systems, inertial navigation, and integration*, chapter Kalman Filter Basics, pages 179-228. John Wiley & Sons, Inc., 2001, the entire contents of which are incorporated herein by reference, often denoted EKF, is one example of an observer as presented in section 1. It has the same form as the general observer in (1.5-1.6) and formulates expressions for P and functions g and m. It can be implemented in continuous, continuous-discrete, or discrete form and in single-rate or multi-rate form. Here, the continuous EKF is presented in section 1.6.1 and the discrete single-rate EKF in section 1.6.2.

1.6.1 Continuous EKF

The continuous EKF corresponds to the continuous form of the observer in section 1.3.1. Equations (1.10) and (1.11) are in this case:

$$\dot{\hat{x}} = f(\hat{x}, u) - L \cdot (h(\hat{x}, u) - y) \quad (1.24)$$

$$\dot{P} = A \cdot P + P \cdot A^T + M \cdot M^T - P \cdot C^T \cdot (N \cdot N^T)^{-1} \cdot C \cdot P \quad (1.25)$$

respectively, where $A = \partial_x f(\hat{x}, u)$ and $C = \partial_x h(\hat{x}, u)$ ($\partial_x$ is the partial derivative with respect to x).

L is calculated according to $$L = P \cdot C^T \cdot (N \cdot N^T)^{-1} \quad (1.26)$$

M and N are tuning matrices chosen by the filter designer.

1.6.2 Discrete Single-rate EKF

The discrete EKF, described in Welch and Bishop, An Introduction to the Kalman Filter, Technical Report TR 95-041 (Updated Jul. 24, 2006) University of North Carolina, Chapel Hill, N.C. 27599, the entire contents of which are incorporated herein by reference, corresponds to the discrete form of the observer in section 1.3.3. The single-rate form is described in section 1.3.4.

1. Prediction:

$$\hat{x}_k^{pred} = f_d(\hat{x}_{k-1}^{corr}, u_k) \quad (1.27)$$

$$P_k^{pred} = \Phi_k \cdot P_{k-1}^{corr} \cdot \Phi_k^T + M \cdot M^T \quad (1.28)$$

2. Update/Correction:

$$L_k = P_k^{pred} \cdot C_k^T (C_k \cdot P_k^{pred} \cdot C_k^T + N \cdot N^T)^{-1} \quad (1.29)$$

$$\hat{x}_k = \hat{x}_k^{pred} - L_k(h_d(\hat{x}_k^{pred}, u_k) - y_k) \quad (1.30)$$

$$P_k^{corr} = (I - L_k \cdot C_k) \cdot P_k^{pred} \quad (1.31)$$

where $\Phi_k = \partial_x f_d(\hat{x}_{k-1}, u_k)$ and $C_k = \partial_x h_d(\hat{x}_k^{pred}, u_k)$.

M and N are tuning matrices chosen by the filter designer.

In the literature, $\hat{x}_k^{pred}$ and $P_k^{pred}$ are often denoted $\hat{x}_k^-$ and $P_k^-$ and $\hat{x}_k^{corr}$ and $P_k^{corr}$ are denoted $\hat{x}_k$ and $P_k$.

1.7 Observer for Data Fusion

An observer can be used for data fusion where data from different sensors is used to calculate the internal state of a system.

When the different sensors have the same sample rates, a single-rate observer can be used (see section 1.3.4). In most cases, the sensors will have different sample rates and a multi-rate observer as presented in section 1.3.5 can be used.

2 Data Fusion of Optical and Inertial Data 2.1 Mathematical Model 2.1.1 Coordinate Systems In one exemplary embodiment, two coordinate systems are used: one is fixed by the camera, the other by the handheld tool or other tracked object.

Figure 11:
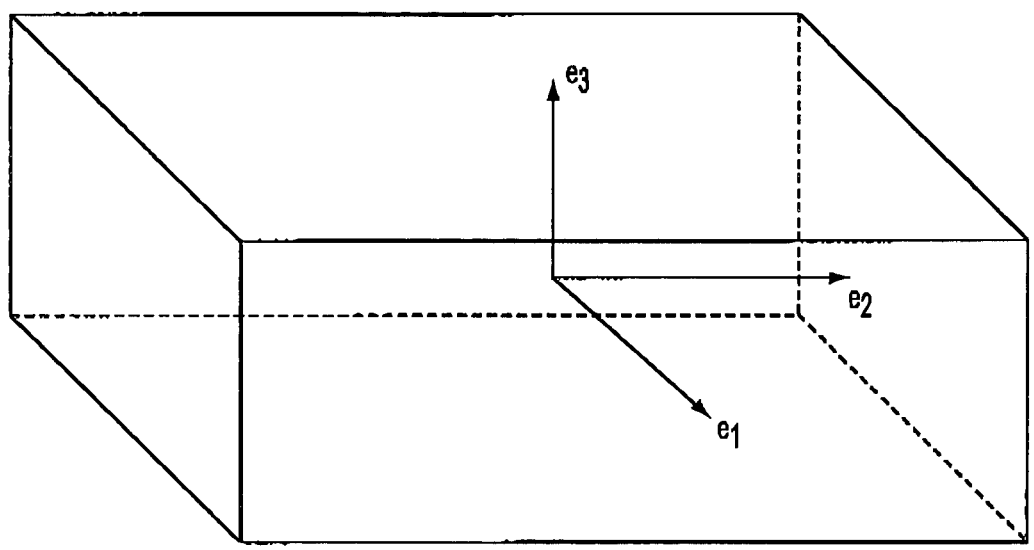
FIG. 11 illustrates a body coordinate system used in one embodiment of an object tracking system according to the present invention.

Body Coordinates: The body coordinates are fixed to the handheld tool or other tracked object, or more precisely to the inertial measuring unit (IMU). It has its origin at the IMU's origin, as shown in FIG. 11. The unit vectors are $e_1, e_2, e_3$. Vectors in body coordinates are marked with an index B.

Figure 12:
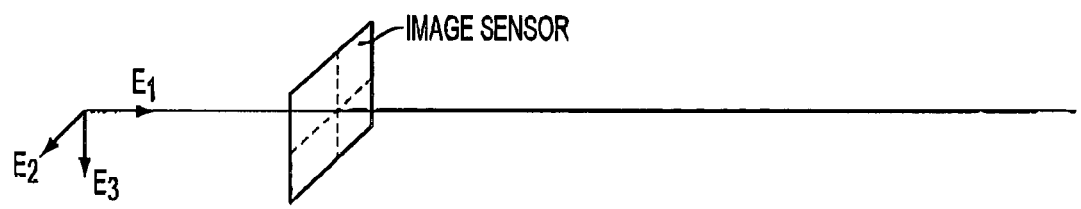
FIG. 12 illustrates a camera coordinate system used in one embodiment of an object tracking system according to the present invention.

Camera Coordinates: The camera coordinates are fixed by the camera (or one of the cameras) and have their origin inside the camera, as shown in FIG. 12. The origin is on the optical axis (E1), at a distance f from the image sensor where f is the camera's focal distance. The unit vectors are $E_1, E_2, E_3$. Vectors in camera coordinates are marked with an index C.

Transformation: vectors can be transformed from body to camera coordinates or vice versa using a quaternion q. A vector $x_B$ in body coordinates can be transformed to camera coordinates by:

$$x_C = q \cdot x_B \cdot q^{-1}$$

2.1.2 Rigid Body Model

Figure 13:
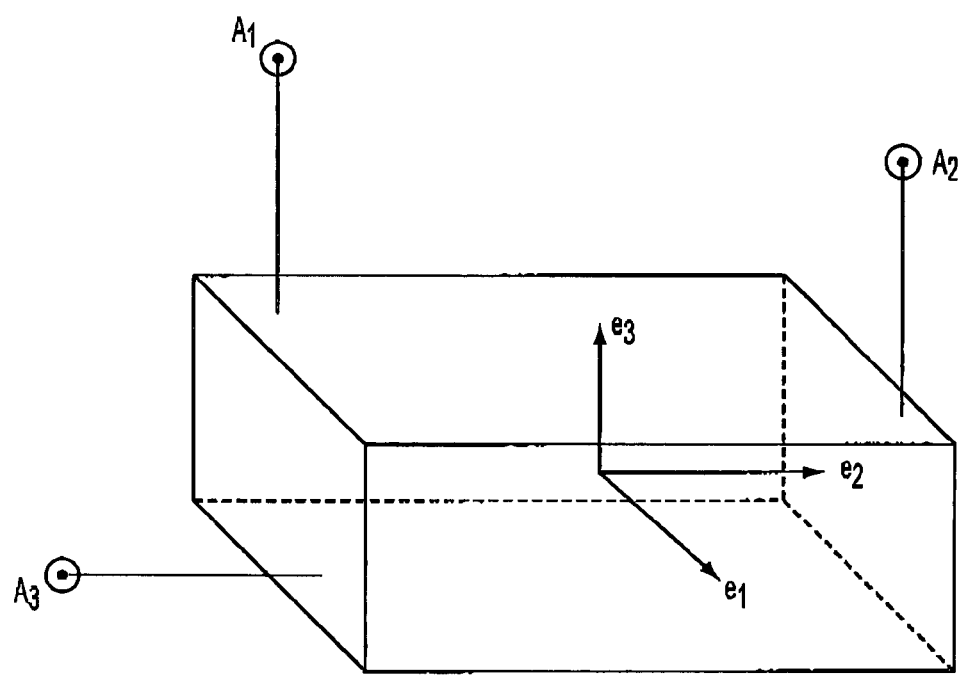
FIG. 13 illustrates one embodiment of a rigid body according to the present invention having three markers and an inertial measuring unit (IMU).

In the description that follows, a Rigid Body is considered having three markers (A1, A2, A3) attached to the IMU, as shown in FIG. 13. The marker positions are given in body coordinates.

$$A_{1B} = \begin{bmatrix} l_{1x} \\ l_{1y} \\ l_{1z} \end{bmatrix}_B = l_{1x} \cdot e_1 + l_{1y} \cdot e_2 + l_{1z} \cdot e_3 \quad (2.1)$$

$$A_{2B} = \begin{bmatrix} l_{2x} \\ l_{2y} \\ l_{2z} \end{bmatrix}_B = l_{2x} \cdot e_1 + l_{2y} \cdot e_2 + l_{2z} \cdot e_3 \quad (2.2)$$

$$A_{3B} = \begin{bmatrix} l_{3x} \\ l_{3y} \\ l_{3z} \end{bmatrix}_B = l_{3x} \cdot e_1 + l_{3y} \cdot e_2 + l_{3z} \cdot e_3 \quad (2.3)$$

To describe the marker positions in camera coordinates, the origin of the body coordinate system is considered as the Rigid Body's position and is called:

$$A_C = \begin{bmatrix} x \\ y \\ z \end{bmatrix}_C = x \cdot E_1 + y \cdot E_2 + z \cdot E_3$$

The marker positions are transformed to camera coordinates using a quaternion:

$$\overrightarrow{OA_{1C}} = \overrightarrow{OA_C} + q \cdot (l_{1x} \cdot e_1 + l_{1y} \cdot e_2 + l_{1z} \cdot e_3) \cdot q^{-1} \quad (2.4)$$

$$\overrightarrow{OA_{2C}} = \overrightarrow{OA_C} + q \cdot (l_{2x} \cdot e_1 + l_{2y} \cdot e_2 + l_{2z} \cdot e_3) \cdot q^{-1} \quad (2.5)$$

$$\overrightarrow{OA_{3C}} = \overrightarrow{OA_C} + q \cdot (l_{3x} \cdot e_1 + l_{3y} \cdot e_2 + l_{3z} \cdot e_3) \cdot q^{-1} \quad (2.6)$$

2.1.3 Camera Model

A pinhole camera model can be used to represent the projection of a point to the image sensor. A point $A_C = [x, y, z]^T$ is projected along the optical axis $E_1$ to a point P on the image sensor (see FIG. 12) according to the following equation:

$$P = \frac{f}{x} \cdot A_C = \frac{f}{x} \cdot \begin{bmatrix} x \\ y \\ z \end{bmatrix}_C = \begin{bmatrix} f \\ f\frac{y}{x} \\ f\frac{z}{x} \end{bmatrix}_C \quad (2.7)$$

$$= \frac{f}{\langle \overrightarrow{OA_C}, E_1 \rangle} \cdot \overrightarrow{OA_C} \quad (2.8)$$

The first coordinate of P is f; this means the image is on the image sensor. The second and third coordinates of P describe the image position on the sensor; they are considered as the "image coordinates."

2.1.4 States, Inputs and, Outputs

The system has 10 states:

3 for the rigid body's position (=point A) in camera coordinates: pos=$[x, y, z]^T$ 3 for the rigid body's velocity in camera coordinates: v=$[v_x, v_y, v_z]^T$.

4 for the quaternion describing the rigid body's orientation: q=$[q_0, q_1, q_2, q_3]^T$ Thus, the system's state vector is X=$[x, y, z, v_x, v_y, v_z, q_0, q_1, q_2, q_3]^T$ The system has 6 inputs:

3 accelerometer measurements: $a_m = [a_x, a_y, a_z]^T$ 3 gyroscope measurements: $\omega_m = [\omega_1, \omega_2, \omega_3]^T$ Thus, the system's input vector is U=$[a_x, a_y, a_z, \omega_1, \omega_2, \omega_3]^T$ The system has 6 outputs (for three markers and one camera); for each marker its 2D coordinates on the camera sensor:

$P_1$ is the image of $A_1$
$P_2$ is the image of $A_2$
$P_3$ is the image of $A_3$ The outputs are:

$y_1$=y coordinate of $P_1$
$y_2$=z coordinate of $P_1$
$y_3$=y coordinate of $P_2$
$y_4$=z coordinate of $P_2$
$y_5$=y coordinate of $P_3$
$y_6$=z coordinate of $P_3$ Thus, the system's output vector is Y=$[y_1, y_2, y_3, y_4, y_5, y_6]^T$ (The number of outputs depends on the number of cameras and markers used. For example, a system with 2 cameras and 3 markers would have 12 outputs—the 3 markers are projected to 2 cameras which give 6 coordinates each.)

2.1.5 Dynamics Equations $$\dot{pos} = v \quad (2.9)$$

$$\dot{v} = G + q \cdot a_m \cdot q^{-1} \quad (2.10)$$

$$\dot{q} = \frac{1}{2} \cdot q \cdot \omega_m \text{ or} \quad (2.11)$$

$$\dot{X} = \begin{bmatrix} v \\ G + q \cdot a_m \cdot q^{-1} \\ \frac{1}{2} \cdot q \cdot \omega_m \end{bmatrix} = f(X, U) \quad (2.12)$$

where G=$[0, 0, g]^T$ with g=9.81 m/s².

2.1.6 Output Equations $$y_1 = \langle \vec{OP_1}, E_2 \rangle = f \cdot \left\langle \frac{\vec{OA_1}}{\langle \vec{OA_1}, E_1 \rangle}, E_2 \right\rangle \quad (2.13)$$

$$y_2 = \langle \vec{OP_1}, E_3 \rangle = f \cdot \left\langle \frac{\vec{OA_1}}{\langle \vec{OA_1}, E_1 \rangle}, E_3 \right\rangle \quad (2.14)$$

-continued $$y_3 = \langle \vec{OP_2}, E_2 \rangle = f \cdot \left\langle \frac{\vec{OA_2}}{\langle \vec{OA_2}, E_1 \rangle}, E_2 \right\rangle \quad (2.15)$$

$$y_4 = \langle \vec{OP_2}, E_3 \rangle = f \cdot \left\langle \frac{\vec{OA_2}}{\langle \vec{OA_2}, E_1 \rangle}, E_3 \right\rangle \quad (2.16)$$

$$y_5 = \langle \vec{OP_3}, E_2 \rangle = f \cdot \left\langle \frac{\vec{OA_3}}{\langle \vec{OA_3}, E_1 \rangle}, E_2 \right\rangle \quad (2.17)$$

$$y_6 = \langle \vec{OP_3}, E_3 \rangle = f \cdot \left\langle \frac{\vec{OA_3}}{\langle \vec{OA_3}, E_1 \rangle}, E_3 \right\rangle \text{ or} \quad (2.18)$$

$$Y = h(X, U) \quad (2.19)$$

The camera's focal distance f and the outputs are given in pixels.

2.2 Extended Kalman Filter for Data Fusion from Optical and Inertial Sensors

There are two types of measurements:

1. Inertial measurements: 3 accelerometer and 3 gyroscope measurements
2. Optical measurements: 3 2D marker images on 1 camera The relationship of the measurements to the system are:

1. The inertial measurements are considered as the system inputs: U=$[a_m, \omega_m]^T$
2. The optical measurements are considered as the system outputs: Y=$[y_1, y_2, y_3, y_4, y_5, y_6]^T$ The rigid body's position, velocity, and orientation are chosen as the system state: X=[position, velocity, orientation]. These are the values that are found with the data fusion algorithm and that are estimated by the EKF. The prediction step calculates an intermediate estimate of the system state (position, velocity, orientation) using the inertial measurements $a_{m,k-1}$ and the previous estimate $\hat{X}_{k-1}$:

$$\hat{X}_k^- = f_d(\hat{X}_{K-1}, a_{m,k-1}, \omega_{m,k-1}) \quad (2.20)$$

$$P_k^- = \Phi_k \cdot P_{k-1} \cdot \Phi_k^T + Q \quad (2.21)$$

Here, the discretized form of the dynamics equations (2.12) is used. The output of this prediction step is the estimate $\hat{X}_k^-$.

The correction step calculates an estimate of the system state (position, velocity, orientation) using the optical measurements $Y_k$ and the state estimate $\hat{X}_k^-$ from the prediction step:

$$L_k = P_k^- \cdot C_k^T (C \cdot P_k^- \cdot C_k^T + R)^{-1} \quad (2.22)$$

$$\hat{Y}_k = h_d(\hat{X}_k^-, U) \quad (2.23)$$

$$\hat{X}_k = \hat{X}_k^- - L_k \cdot (\hat{Y}_k - Y_k) \quad (2.24)$$

$$P_k = (I - L_k \cdot C_k) \cdot P_k^- \quad (2.25)$$

The output of this update step is the final state estimate $\hat{X}_k$.

Timing of EKF steps: The timing of the prediction and update steps is an important point when using an EKF for data fusion. The two steps are not always executed one after the other but the timing depends on the sample rates of the inertial and the optical data. The inertial sensor defines the execution times of the prediction steps, the optical sensor those of the corrections steps. Since inertial sensors usually have a much higher sample rates than optical sensors, the EKF presented here would make more predictions than corrections. Consequently, several prediction steps would be carried between two correction steps.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for tracking motion of an object comprising:
an object comprising a plurality of optical markers rigidly connected to the object and an inertial transmitter for transmitting high speed signals of object movement;
at least one camera for imaging said plurality of markers and generating image data indicative of the object location;
a receiver for receiving inertial movement signals from the inertial transmitter; and
a processor for executing an estimation algorithm, the estimation algorithm merging the optically-derived image data and the high speed inertial movement signals to generate estimated motion data at a frequency of 300-500 Hz, wherein the estimation algorithm is a multiplicative extended kalman filter and operates directly on raw image data comprising a plurality of two dimensional pixel coordinates.

2. The system of claim 1, wherein the estimated motion data comprises a position of the object, a velocity of the object, and an orientation of the object.

3. The system of claim 1, wherein the inertial transmitter further comprises gyroscopic and accelerometer sensors to provide six degrees of movement tracking.

4. The system of claim 3, wherein the estimation algorithm only receives as inputs a plurality of two-dimensional pixel coordinates, a set of sensor readings generated by the gyroscopic and accelerometer sensors, and previously generated estimated motion data.

5. The system of claim 1, wherein the object further comprises at least three markers.

6. The system of claim 1, wherein the object further comprises at least four markers.

7. The system of claim 1, wherein the system comprises at least two cameras.

8. The system of claim 1, wherein the object includes a mating element for mating the object to another instrument.

9. The system of claim 1, wherein the inertial movement signals are generated at a sample rate that is at least three times a sample rate of the location signals generated by the camera.

10. The system of claim 1, further comprising a servo-control configured to adjust at least one of a position, a velocity, and an orientation of the object.

11. The system of claim 10, wherein the servo-control compensates for a motion disturbance detected from the estimated motion data by adjusting at least one of the position, the velocity, and the orientation of the object.

12. A method for locating a moving object, comprising:
receiving, at a first sample rate, image data from at least one camera, said data representing at least one image of an object having a plurality of optical markers mounted thereto;
receiving, at a second higher sample rate, inertial movement signals from an inertial sensor coupled to the object; and
using an estimation algorithm to generate estimated motion data of the object by merging the image data and the inertial movement signals
wherein the estimation algorithm is a multiplicative extended kalman filter and operates directly on new image data comprising a plurality of two-dimensional pixel coordinates.

13. The method of claim 12, wherein the step of using an estimation algorithm to generate estimated motion data is performed at the second sample rate.

14. The method of claim 12, wherein the second sample rate is 300-500 Hz.

15. The method of claim 12, wherein the estimated motion data comprises a position of the object, a velocity of the object, and an orientation of the object.

16. The method of claim 12, wherein the estimation algorithm only receives as inputs a plurality of two-dimensional pixel coordinates, the inertial movement signals, and previously generated estimated motion data.

17. The method of claim 12, further comprising actuating a servo-control to adjust at least one of a position, a velocity, and an orientation of the object in response to a disturbance detected from the estimated motion data.

18. A system for navigated surgery comprising:
a surgical tool comprising a plurality of optical markers rigidly connected to the surgical tool and an inertial transmitter for transmitting high speed signals of tool movement;
at least one camera for imaging said plurality of markers and generating image data indicative of the tool location;
a receiver for receiving inertial movement signals from the inertial transmitter;
a processor for executing an estimation algorithm, the estimation algorithm merging the optically-derived image data and the high speed inertial movement signals to generate estimated motion data at a frequency of 300-500 Hz, wherein the estimation algorithm is a multiplicative extended kalman filter and operates directly on raw image data comprising a plurality of two-dimensional pixel coordinates.

19. The system of claim 18, wherein the estimated motion data comprises a position of the tool, a velocity of the tool, and an orientation of the tool.

20. The system of claim 18, wherein the inertial transmitter further comprises gyroscopic and accelerometer sensors to provide six degrees of movement tracking.

21. The system of claim 20, wherein the estimation algorithm only receives as inputs a plurality of two-dimensional pixel coordinates, a set of sensor readings generated by the gyroscopic and accelerometer sensors, and previously generated estimated motion data.

22. The system of claim 18, wherein the tool further comprises at least three markers.

23. The system of claim 18, wherein the tool further comprises at least four markers.

24. The system of claim 18, wherein the system comprises at least two cameras.

25. The system of claim 18, wherein the tool includes a mating element for mating the tool to another instrument.

26. The system of claim 18, wherein the inertial movement signals are generated at a sample rate that is at least three times a sample rate of the location signals generated by the camera.

27. The system of claim 18, further comprising a servo-control configured to adjust at least one of a position, a velocity, and an orientation of the surgical tool.

28. The system of claim 27, wherein the servo-control compensates for a motion disturbance detected from the estimated motion data by adjusting at least one of the positon, the velocity, and the orientation of the surgical tool.

* * * * *